(12) United States Patent
Mickley et al.

(10) Patent No.: US 7,695,455 B2
(45) Date of Patent: Apr. 13, 2010

(54) DELIVERY OF A LOW VOLUME LIQUID BOLUS

(75) Inventors: Timothy J. Mickley, Elk River, MN (US); Thomas R. Hektner, Medina, MN (US); Louis Ellis, St. Anthony, MN (US); Gary L. Hendrickson, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1478 days.

(21) Appl. No.: 10/882,397

(22) Filed: Jul. 2, 2004

(65) Prior Publication Data

US 2004/0243098 A1    Dec. 2, 2004

Related U.S. Application Data

(63) Continuation of application No. 09/138,131, filed on Aug. 21, 1998, now Pat. No. 6,764,461, which is a continuation-in-part of application No. 08/982,220, filed on Dec. 1, 1997, now Pat. No. 6,050,986.

(51) Int. Cl.
*A61M 5/178* (2006.01)
*A61M 5/24* (2006.01)
*A61M 5/00* (2006.01)

(52) U.S. Cl. .................. 604/212; 604/200; 604/244
(58) Field of Classification Search .......... 604/500, 604/288.01–288.04, 200–206, 212, 213
See application file for complete search history.

(56) References Cited

U.S. PATENT DOCUMENTS

| | | | |
|---|---|---|---|
| 2,514,576 A * | 7/1950 | Hein et al. ............. | 604/212 |
| 4,085,749 A * | 4/1978 | Chambron ............. | 604/143 |
| 4,578,061 A | 3/1986 | Lemelson | |
| 4,790,819 A | 12/1988 | Li et al. | |
| 5,186,431 A | 2/1993 | Tamari | |
| 5,306,246 A | 4/1994 | Sahatjian et al. | |
| 5,358,493 A | 10/1994 | Schweich, Jr. et al. | |
| 5,391,183 A | 2/1995 | Janzen et al. | |
| 5,437,631 A | 8/1995 | Janzen | |

(Continued)

FOREIGN PATENT DOCUMENTS

EP    202 658 A1  *  11/1986

(Continued)

*Primary Examiner*—Nicholas D Lucchesi
*Assistant Examiner*—Victoria P Campbell
(74) *Attorney, Agent, or Firm*—Vidas, Arrett & Steinkraus

(57) ABSTRACT

A catheter system includes a catheter having a proximal end, a distal end, and a lumen extending therein. An administering portion is disposed at the distal end of the catheter and is configured to administer a bolus of liquid in response to positive pressure in a distal portion of the lumen. The catheter system of the present invention has a dead space of less 0.32 cc and preferably less than 0.15 cc in which residual therapeutic agents remain after delivery. The present invention also includes a method of administering a liquid to a treatment site. The distal end of the catheter is transluminally positioned proximate the treatment site. The catheter is charged by placing a bolus of the liquid in the lumen. A positive pressure is created to drive the bolus to the administering tip to express the bolus from the distal end of the catheter.

10 Claims, 14 Drawing Sheets

U.S. PATENT DOCUMENTS

| | | |
|---|---|---|
| 5,545,133 A | 8/1996 | Burns et al. |
| 5,558,642 A | 9/1996 | Schweich, Jr. et al. |
| 5,569,201 A * | 10/1996 | Burns .................... 604/102.02 |
| 5,649,959 A | 7/1997 | Hannam et al. |
| 5,702,384 A | 12/1997 | Umeyama |
| 5,746,728 A | 5/1998 | Py |
| 5,766,157 A | 6/1998 | Tilton, Jr. |
| 5,772,629 A | 6/1998 | Kaplan |
| 5,807,311 A | 9/1998 | Palestrant |
| 5,820,610 A | 10/1998 | Baudino |
| 5,833,658 A | 11/1998 | Levy et al. |
| 5,840,061 A | 11/1998 | Menne et al. |
| 5,845,646 A | 12/1998 | Lemelson |
| 5,848,993 A * | 12/1998 | Tanhehco et al. ........... 604/217 |
| 6,050,986 A | 4/2000 | Hektner |
| 6,524,305 B1 * | 2/2003 | Peterson et al. .......... 604/892.1 |

FOREIGN PATENT DOCUMENTS

| | | |
|---|---|---|
| EP | 0 202 658 | 4/1989 |
| WO | WO 98/10824 * | 3/1998 |

\* cited by examiner

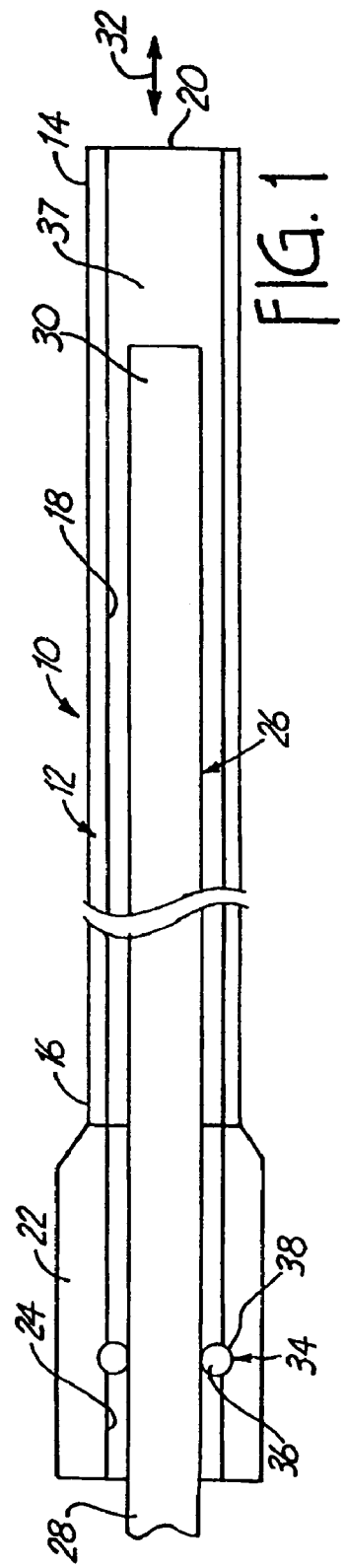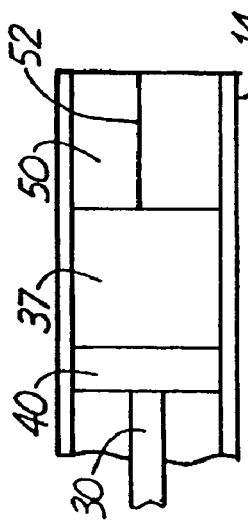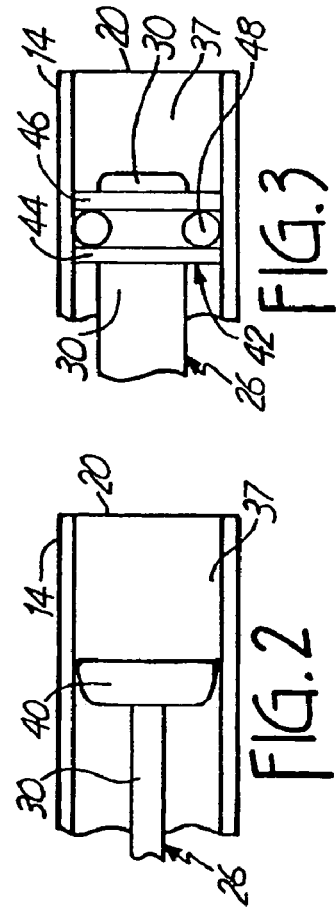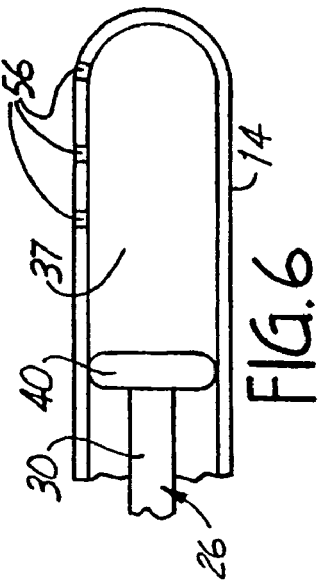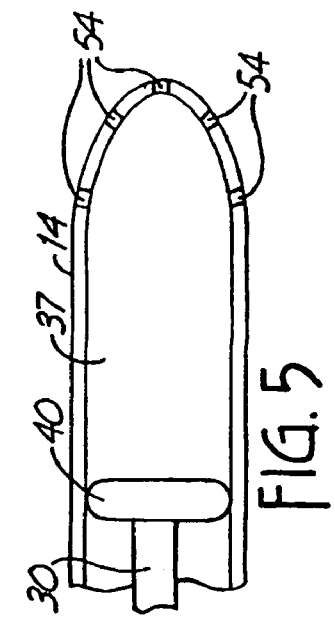

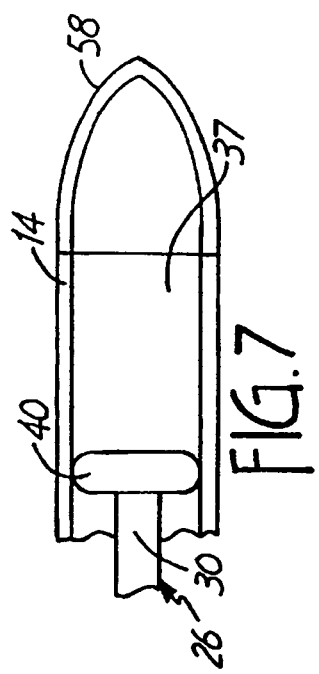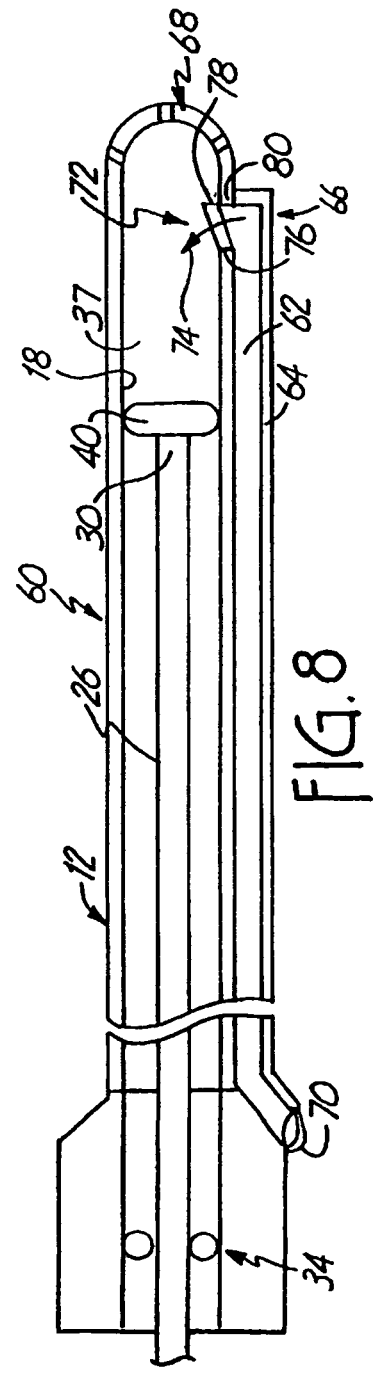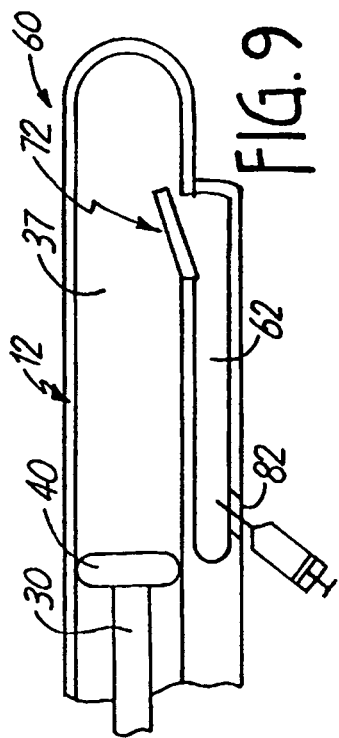

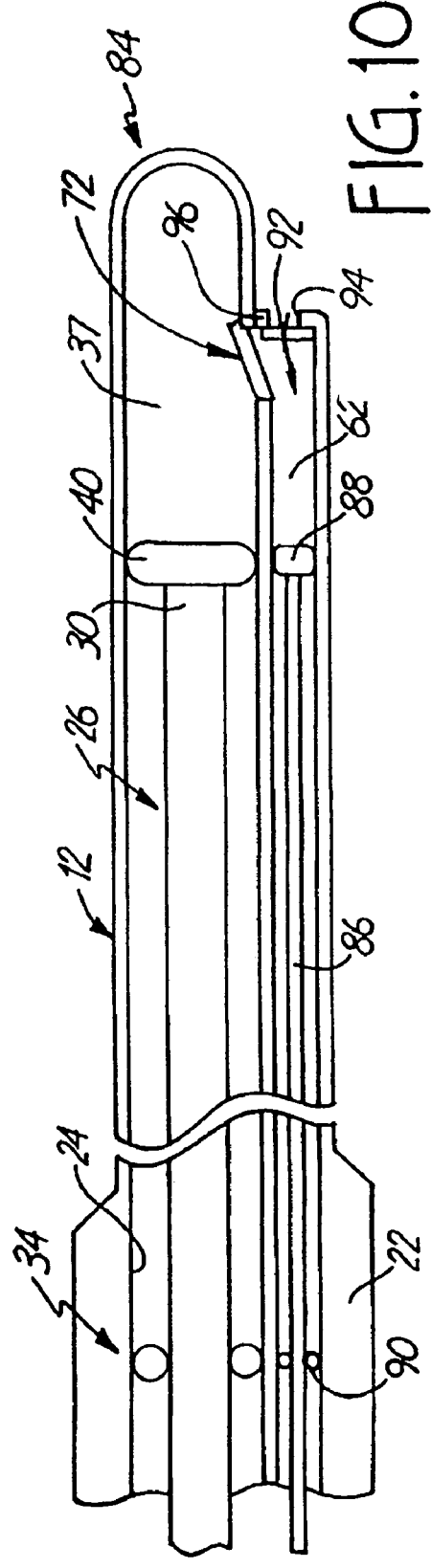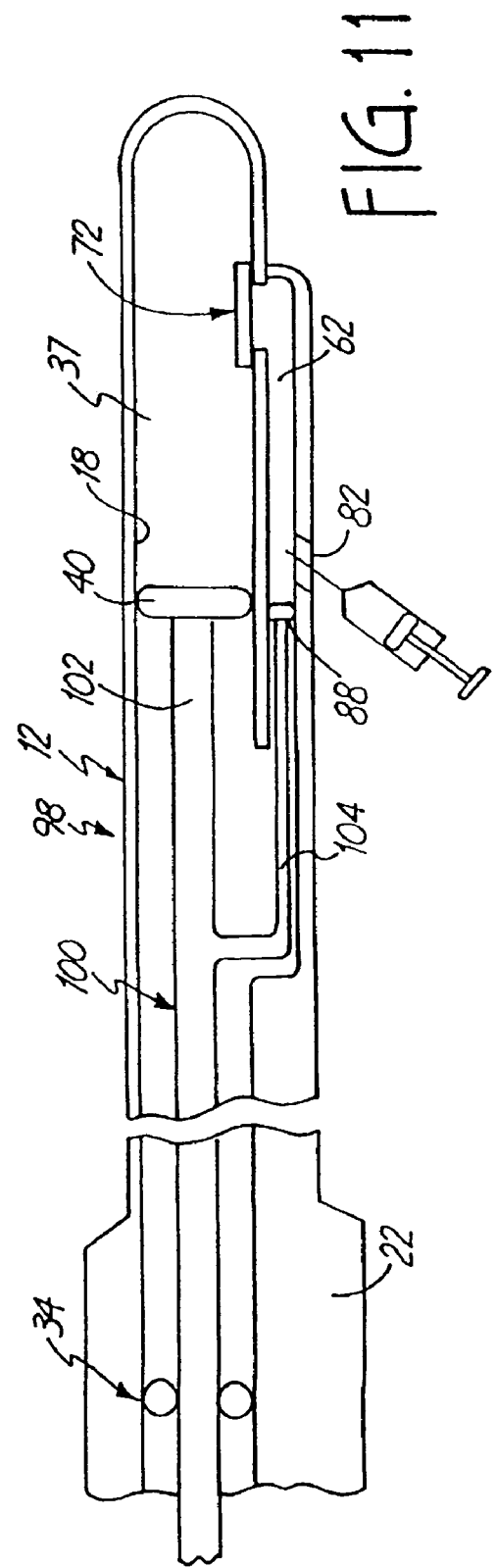

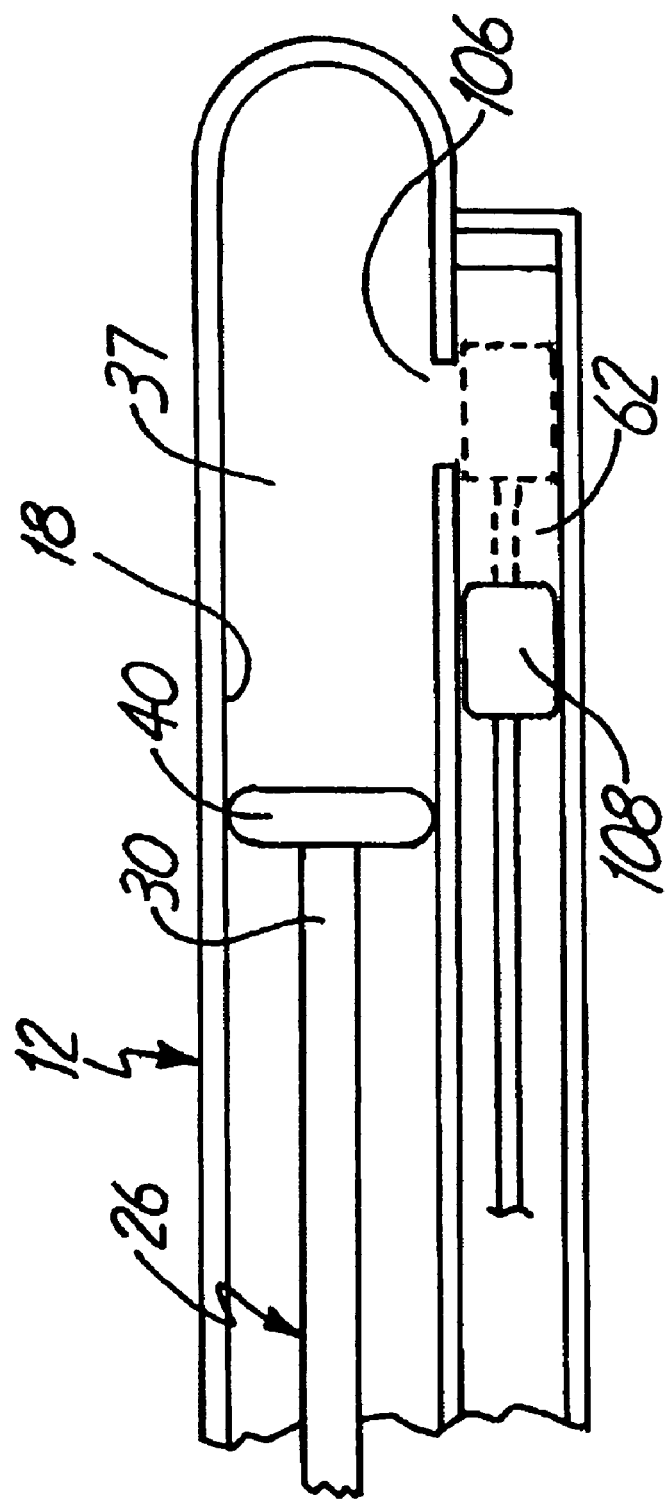

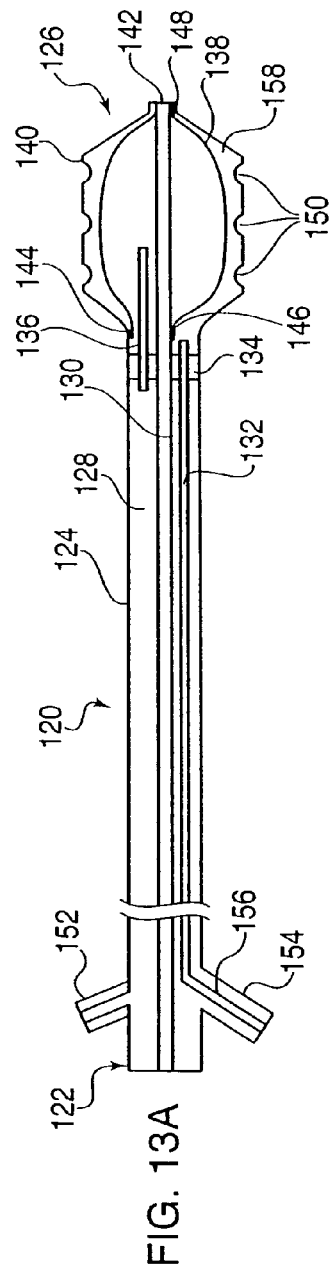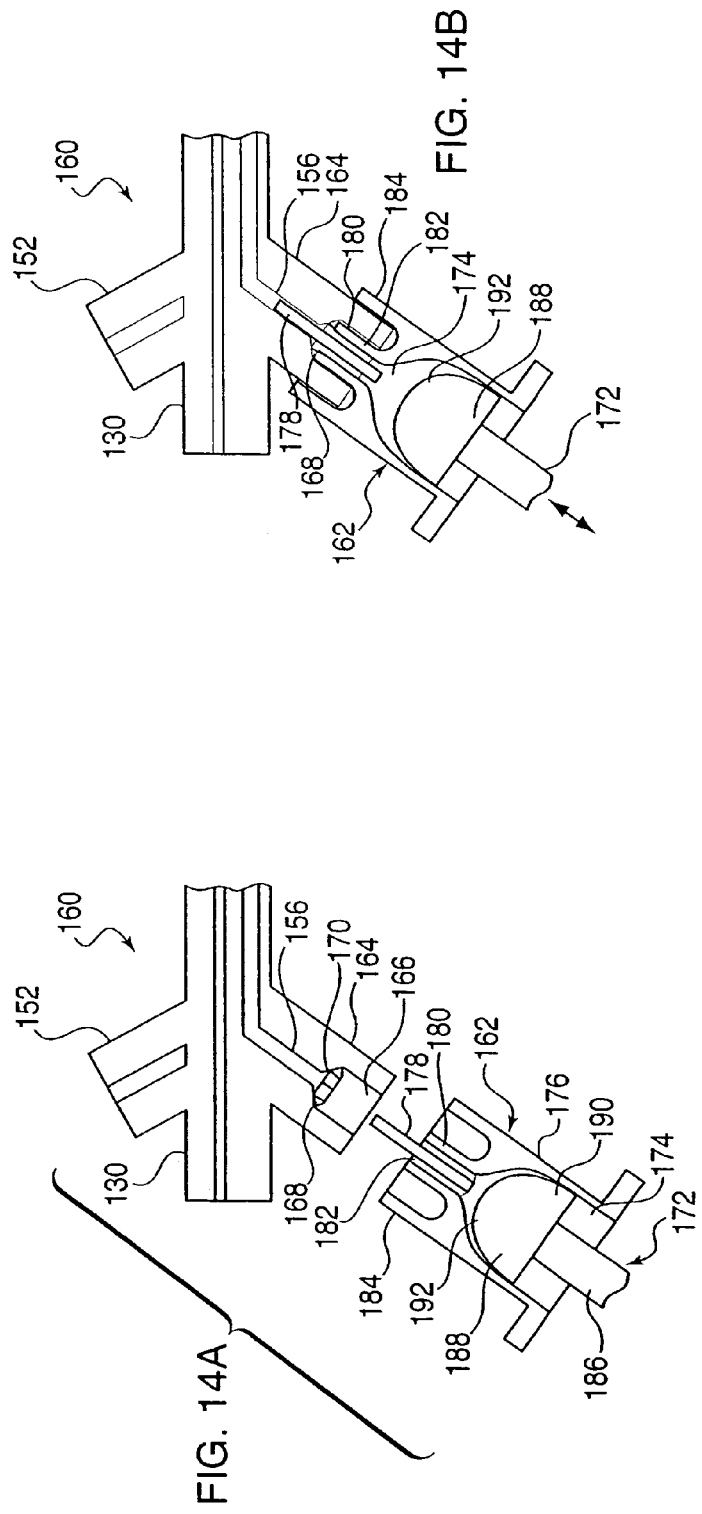
FIG. 13A
FIG. 14A
FIG. 14B

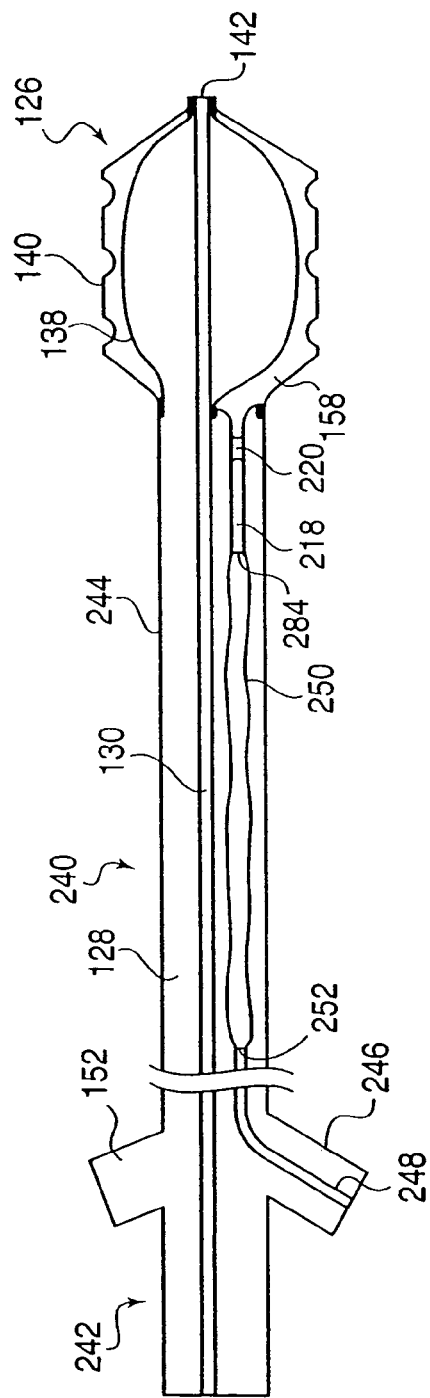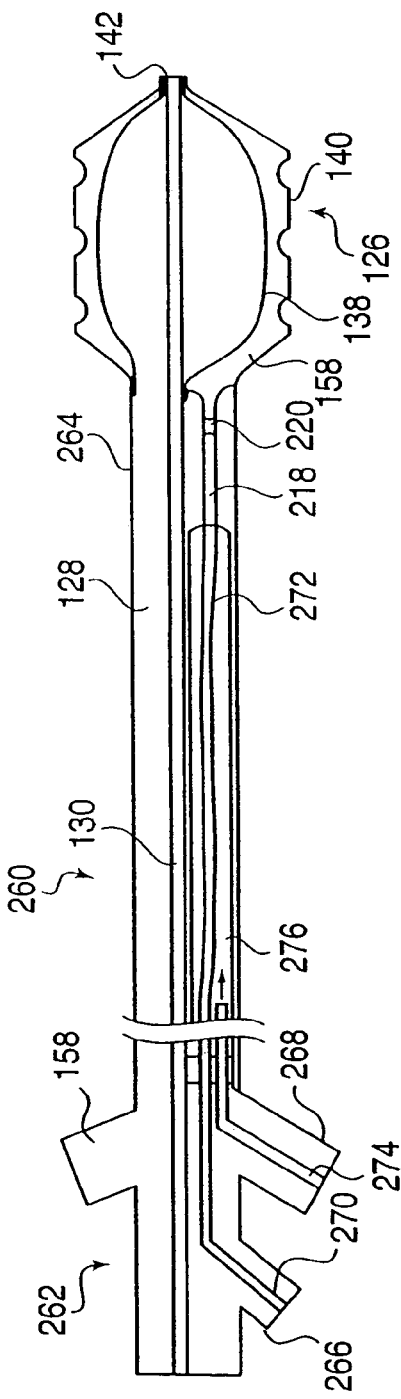

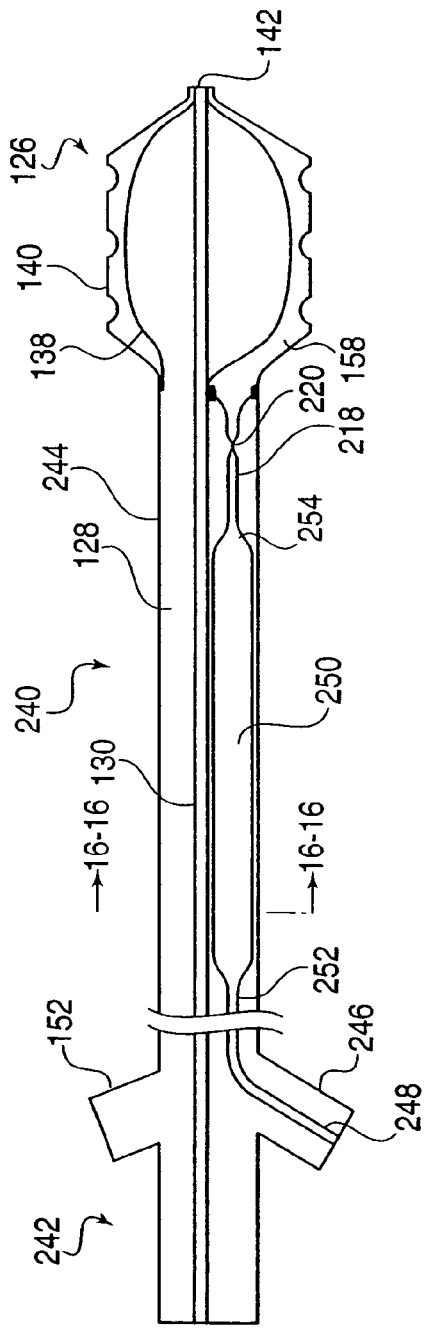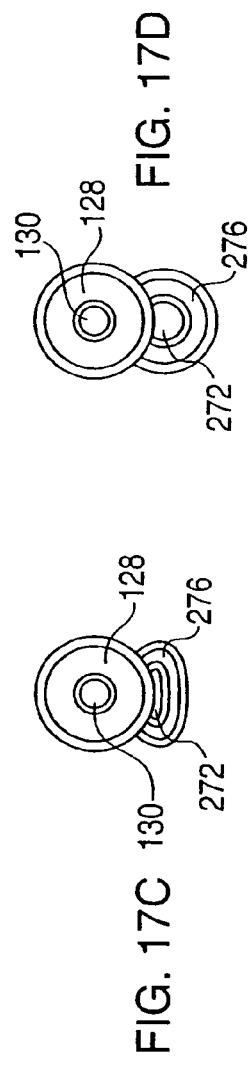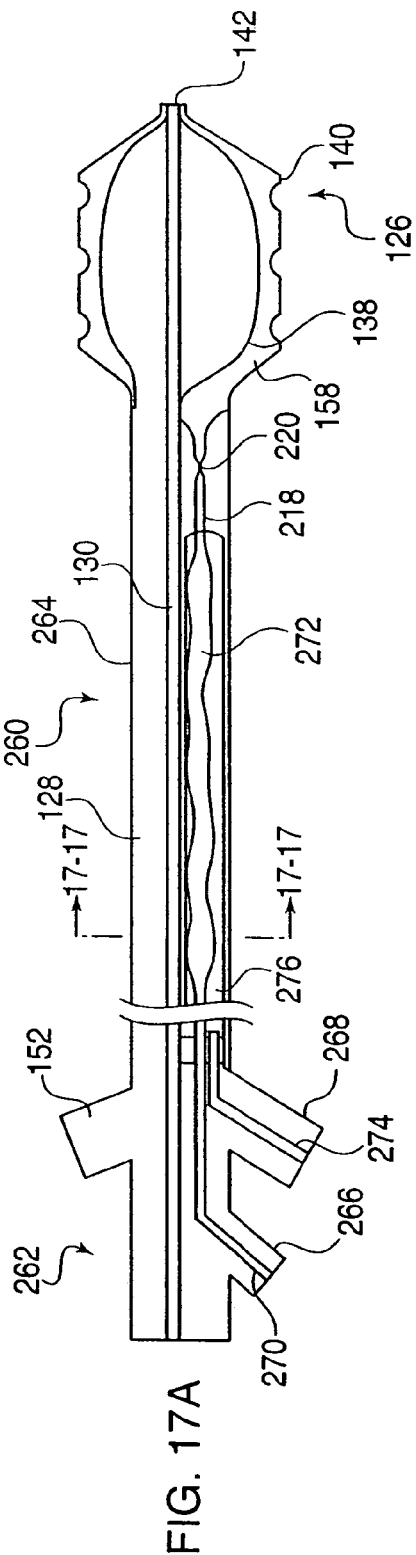

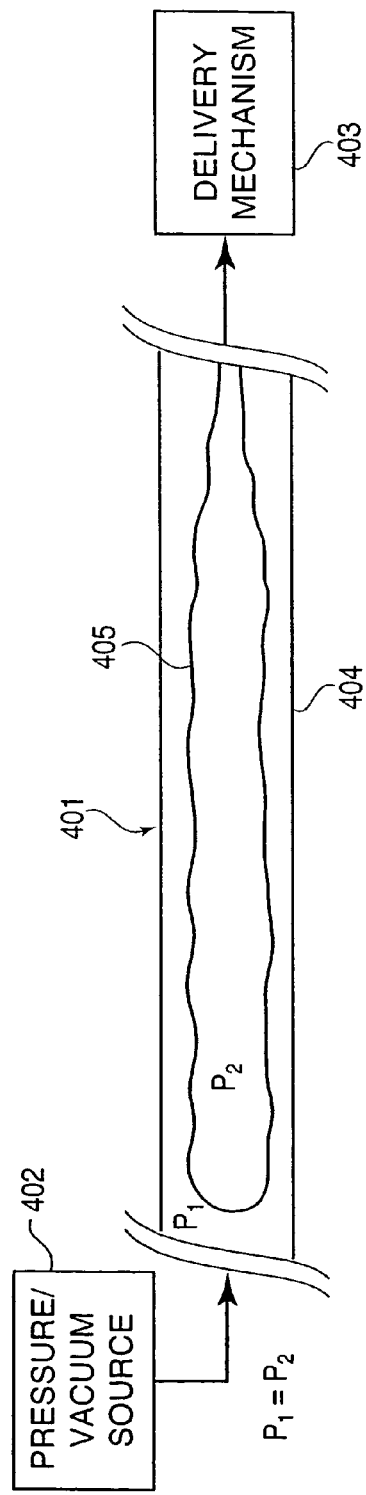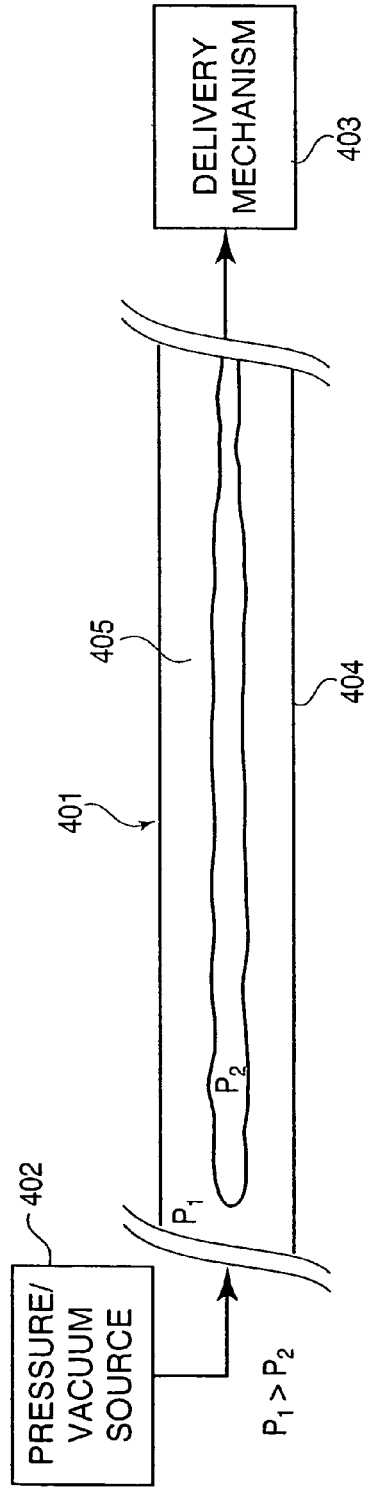

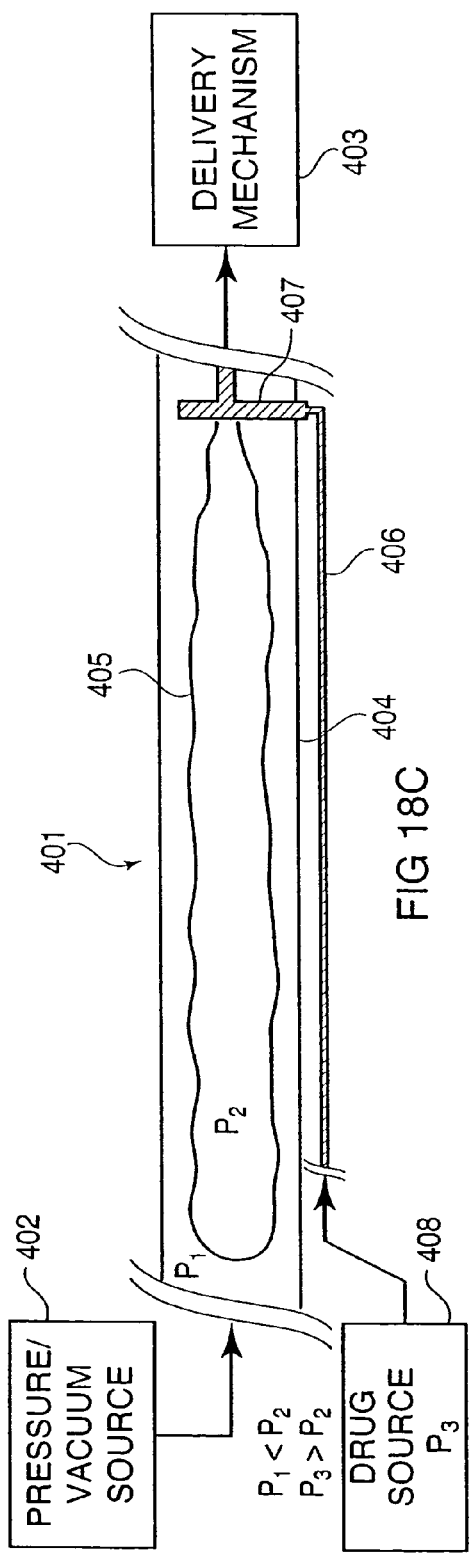
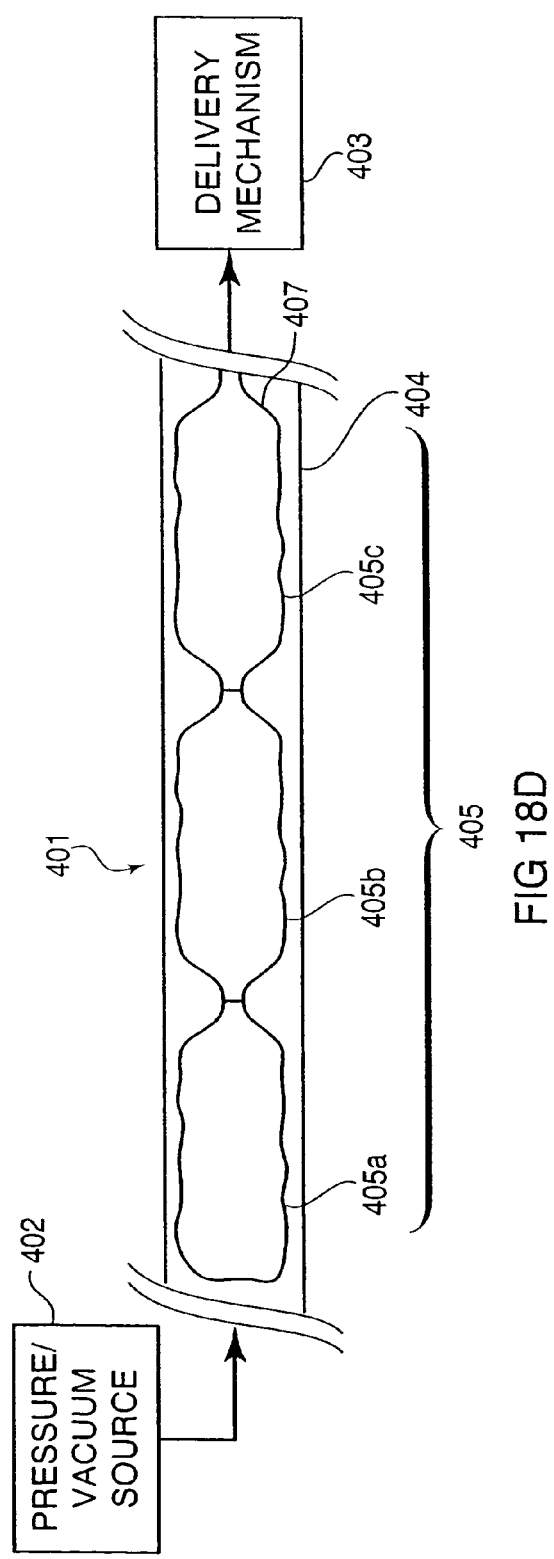

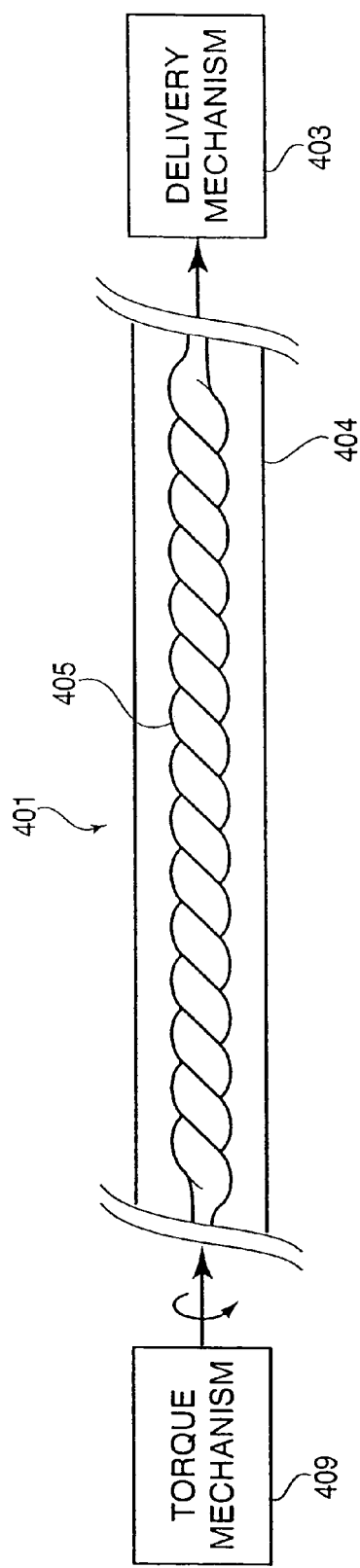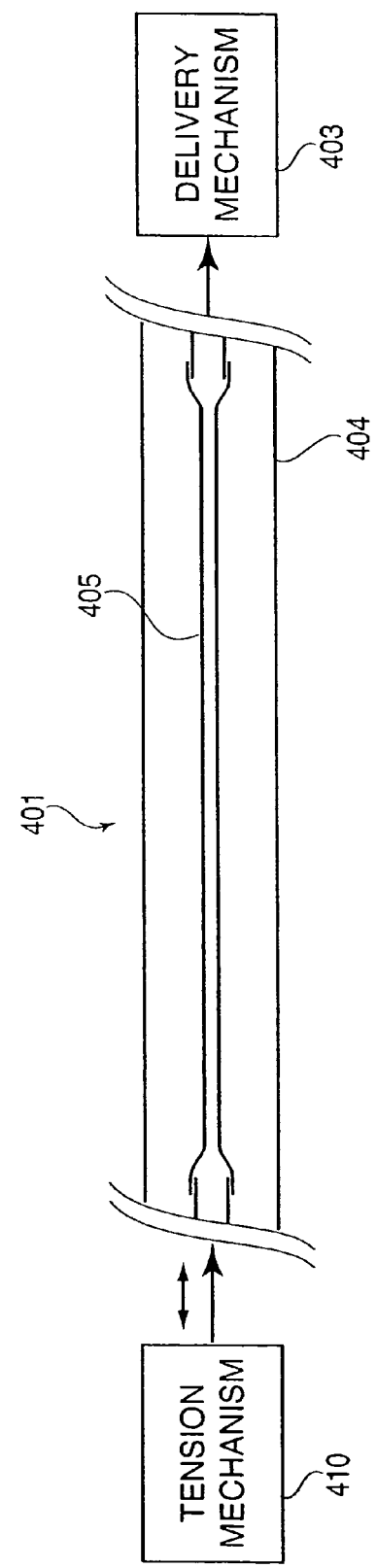
FIG 18E
FIG 18F

DELIVERY OF A LOW VOLUME LIQUID BOLUS

REFERENCE TO CO-PENDING APPLICATIONS

The present invention is a continuation of U.S. patent application Ser. No. 09/138,131, filed Aug. 21, 1998 entitled CATHETER SYSTEM FOR THE DELIVERY OF A LOW VOLUME LIQUID BOLUS, now U.S. Pat. No. 6,764,461, which is a continuation-in-part application of U.S. patent application Ser. No. 08/982,220 filed on Dec. 1, 1997 entitled CATHETER SYSTEM FOR THE DELIVERY OF A LOW VOLUME LIQUID BOLUS, now U.S. Pat. No. 6,050,986, assigned to the same assignee as the present application, the entire disclosure of which is hereby incorporated by reference.

INCORPORATION BY REFERENCE

Reference is made to the following co-pending patent applications which are hereby fully incorporated by reference:

U.S. patent Ser. No. 08/308,025, filed on Sep. 16, 1994 entitled "BALLOON CATHETER WITH IMPROVED PRESSURE SOURCE";

U.S. patent Ser. No. 08/586,514 filed on Jan. 16, 1996 entitled "BALLOON CATHETER WITH IMPROVED PRESSURE SOURCE";

U.S. patent Ser. No. 08/619,375 filed on Mar. 21, 1996 entitled "BALLOON CATHETER WITH IMPROVED PRESSURE SOURCE"; and U.S. patent Ser. No. 08/812,390 filed on Mar. 5, 1997 entitled "BALLOON CATHETER WITH IMPROVED PRESSURE SOURCE.

All of the above-referenced patent applications are assigned to the same assignee as the present application.

BACKGROUND OF THE INVENTION

The present invention deals with catheters. More specifically, the present invention deals with delivery of a small bolus of liquid with a catheter.

A wide variety of different mechanisms and techniques have been developed in order to treat coronary disease. However, such techniques and devices are typically drawn to the physical manipulation of biological tissues, such as heart tissue, or other vascular tissue within the vascular system.

For example, some treatment techniques are drawn to the physical removal or dilation of restrictions (stenoses and total occlusions) in the vasculature. Techniques for dealing with this type of disease have included percutaneous transluminal coronary angioplasty (PTCA) in which an angioplasty balloon catheter is inserted into the body via the femoral artery and positioned across a restriction in an artery. The balloon is inflated to widen the restriction and restore blood flow to portions of the heart muscle previously deprived of oxygenated blood. Implantation of stents using PTCA is also a common technique for opening an arterial restriction.

Another technique for dealing with vascular disease includes coronary artery bypass graft (CABG) procedures. Such procedures typically include the placement of a graft at a desired location in the vasculature to supplement blood flow to the area previously deprived of blood (or provided with reduced blood flow) due to the vascular restriction. One common type of CABG procedure involves placement of a saphenous vein graft (SVG) between the ascending aorta proximal of the restriction, and a region in the restricted vessel distal of the restriction.

Another technique for dealing with vascular disease includes an atherectomy procedure. In an atherectomy procedure, an atherectomy device is placed in the vasculature proximate the restriction. The atherectomy device is deployed to physically cut away, abrade, or otherwise physically remove, the occlusive material from the restricted vessel. The portions of the restriction which are severed by the atherectomy device are subsequently removed by aspiration, or by another suitable device.

Another technique called transluminal myocardial revascularization is also receiving attention in the medical community as an acceptable therapy.

Various drug therapies have also been developed. Such therapies have been used in place of, and in conjunction with, the above mentioned therapies under certain circumstances. For example, during grafting procedures, it may be desirable to deliver drugs to the graft site which inhibit the formation of thrombus. In addition, some drug therapies have been developed which involve the delivery of drugs directly to the heart tissue. With recent advancements in the pharmaceutical industry, other drug therapies have also become desirable. Some such recent pharmaceutical developments include the development of gene therapy drugs, such as growth factors.

A transluminal technique for delivering the drugs, along with the various types of known positioning and visualization techniques commonly used with transluminal treatments, can be highly desirable. The drug therapies typically require site specific administration of the drug. Transluminal techniques can be effectively used to deliver a liquid material to a selected site in the vasculature.

However, drug therapies, can be prohibitively expensive. For example, newly developed drugs are commonly extremely expensive and can only be administered in any pragmatic fashion in very low volumes. Typically, such drugs only need to be administered to the vascular site being treated. However, there is no technique available to date by which the site to be treated can be accessed transluminally with a catheter and which enables only a very small quantity of drug to be delivered from the distal portion of the catheter to the treatment site.

Rather, conventional transluminal drug delivery catheters require a proximal infusion device which is connected to a proximal end of the infusion catheter and which is used to pressurize a fluid or infusate which contains the drug to be delivered. The catheter is filled with the infusate and the drug is administered at the distal portion of the infusion catheter (upon pressurization of the infusate) after the catheter is inserted and properly positioned. While the internal volume of such infusion catheters is typically small, it is still much too large to make drug delivery with extremely expensive drugs practical.

SUMMARY OF THE INVENTION

The present invention is drawn to the delivery of a low volume bolus of drug or other treatment material to the myocardium, a vessel, or any other organ or area for which transluminal access is desirable. For example, anti-arrhythmia drugs may be injected into the myocardium using the present invention for electrophysiological therapy. Also, growth factors and other gene therapy substances can be injected into the myocardium for myocardial revascularization.

In one embodiment, the catheter system includes a catheter having a proximal end, a distal end, and a lumen extending therein. An elongate member slidably disposed in the lumen has a distal end located proximate the distal end of the catheter. An administering portion is disposed at the distal end of the catheter and is configured to express a bolus of liquid in response to positive pressure in a distal portion of the lumen created by movement of the elongate member distally in the lumen.

The present invention provides a drug delivery catheter having a minimal dead space so as to minimize the amount of residual drug left in the catheter after administering the drug. Preferably, the drug delivery catheter of the present invention provides a dead space of less that 0.32 cc, including the dead space in the proximal manifold and the remainder of the catheter. More preferably, the drug delivery catheter of the present invention provides a dead space less than 0.15 cc, and ideally less than 0.08 cc.

The present invention also includes a method of administering a liquid to a treatment site. A catheter, having a proximal end, a distal end and a lumen extending therein, as well as an elongate member, slidably disposed in the lumen, are provided. The distal end of the catheter is transluminally positioned proximate the treatment site. The catheter is charged by placing a bolus of the liquid in a distal end of the lumen between a distal end of the catheter and a distal end of the elongate member. The elongate member is then moved distally within the lumen to express the bolus from the distal end of the catheter.

Also, the present device should not be limited to implementation using only conventional catheters per se, but also contemplates any steerably, maneuverable syringe structure. Thus, the term catheter should be construed to include both conventional catheters and elongate, maneuverable syringe structures suitable for maneuvering, manipulation, tracking and steering within a vessel.

The catheter system can be navigated through several lumens and cavities within the body. Intravascular access by the femoral, brachial and radial arteries is contemplated for accessing target sites within the heart or peripheral vasculature. Alternatively, the catheter may be navigated into the ventricles of the heart by way of the aorta for direct treatment of the heart muscle (myocardium). Yet another alternative for accessing the heart chamber is via the vena cava. Lastly, nonvascular ducts or lumens within the body can be accessed for drug delivery such as for cancer treatment.

In accordance with another embodiment of the present invention, a collapsible drug reservoir is included in the catheter and is collapsed to administer the bolus of liquid.

BRIEF DESCRIPTION OF THE DRAWINGS

FIG. 1 is a side sectional view of a catheter system in accordance with one preferred embodiment of the present invention.

FIG. 2 is an enlarged side sectional view of a second embodiment of a distal portion of the catheter system in accordance with the present invention.

FIG. 3 is an enlarged view of the distal end of a catheter system in accordance with another preferred embodiment of the present invention.

FIG. 4 is an enlarged side sectional view of another embodiment of a distal portion of the catheter system in accordance with the present invention.

FIG. 5 is an enlarged side sectional view of another embodiment of a distal portion of the catheter system in accordance with the present invention.

FIG. 6 is an enlarged side sectional view of another embodiment of a distal portion of the catheter system in accordance with the present invention.

FIG. 7 is an enlarged side sectional view of another embodiment of a distal portion of the catheter system in accordance with the present invention.

FIG. 8 is a side sectional view of another embodiment of a catheter system in accordance with the present invention.

FIG. 9 is a side sectional view of the catheter system of FIG. 8, with a modified liquid reservoir configuration.

FIG. 10 is a side sectional view of a catheter system in accordance with one aspect of the present invention, deploying a two piston arrangement.

FIG. 11 is a side sectional view of a catheter system in accordance with one aspect of the present invention utilizing a bifurcated piston configuration.

FIG. 12 is a side sectional view of a catheter system in accordance with one aspect of the present invention utilizing a valve and engageable valve seat configuration.

FIG. 13A is a side sectional view of a catheter system in accordance with another preferred embodiment of the present invention.

FIGS. 14A-14D illustrate a syringe and proximal manifold in accordance with another aspect of the present invention.

FIGS. 16A-16D illustrate the operation of a catheter having a collapsible reservoir in accordance with another aspect of the present invention.

FIGS. 17A-17D illustrate operation of a catheter having a collapsible reservoir in accordance with another aspect of the present invention.

FIGS. 18A-18H illustrate, in schematic form, another embodiment of the present invention utilizing a collapsible membrane.

DETAILED DESCRIPTION OF THE PREFERRED EMBODIMENTS

Figure 13B:
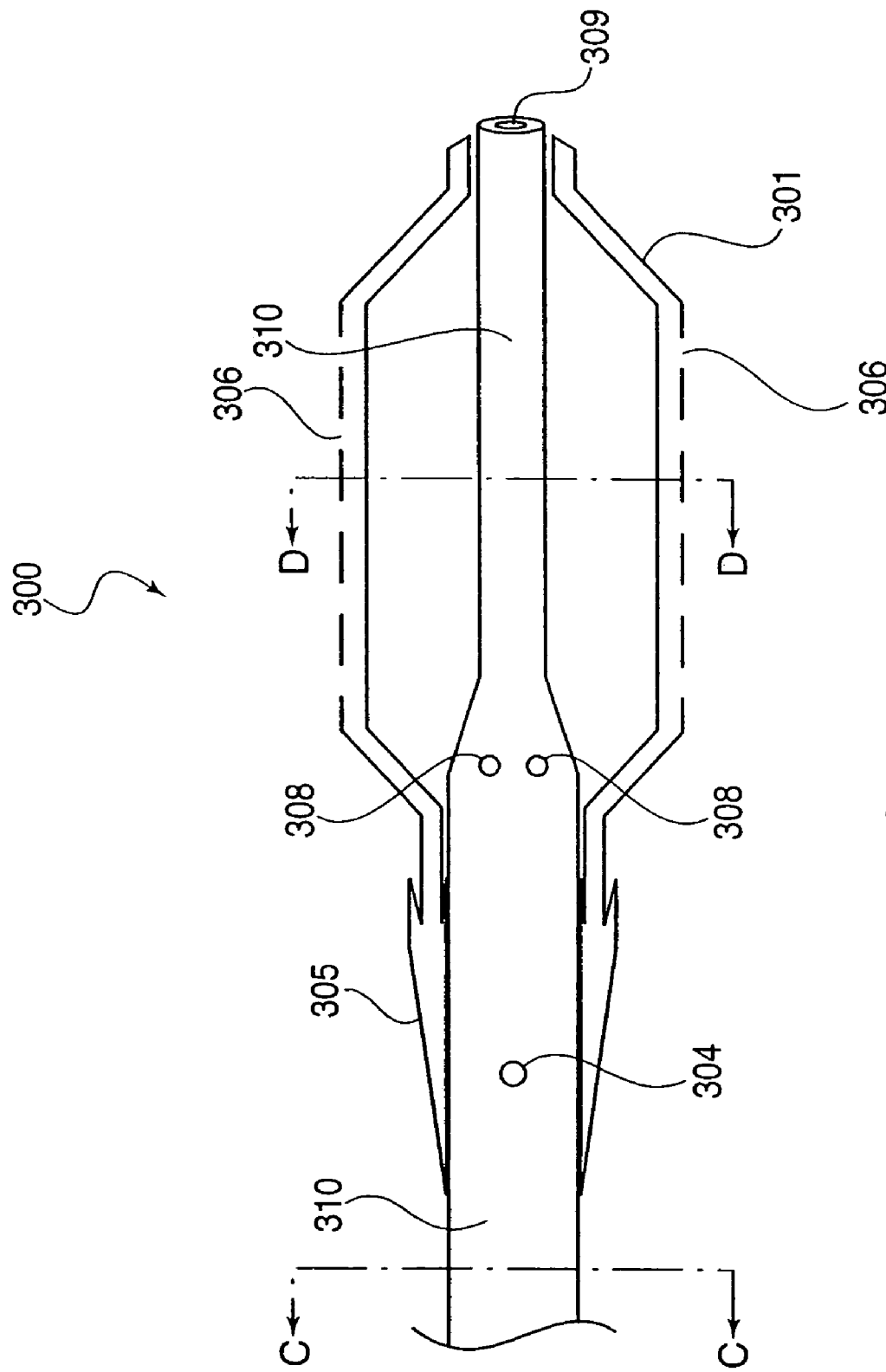
FIG. 13B is a side sectional view of a catheter system in accordance with another preferred embodiment of the present invention utilizing an alternative balloon structure.

FIG. 1 is a side sectional view of a catheter system 10 in accordance with one preferred embodiment of the present invention. Catheter system 10 includes catheter 12 having a distal end 14 and a proximal end 16 and a lumen 18 running therethrough. In the embodiment shown in FIG. 1, distal end 14 is simply an open end providing distal opening 20, and proximal end 16 is coupled to proximal manifold 22 in any known conventional manner.

Manifold 22 preferably has a lumen 24 extending therethrough which is coaxial with lumen 18. Lumen 24 is also preferably in fluid communication with lumen 18.

System 10 also preferably includes piston rod 26. Piston rod 26 is preferably an elongate member which extends from a proximal end 28 (which preferably extends to a region proximal of manifold 22) to a distal end 30 which is preferably proximate distal end 14 of catheter 12. Piston rod 26 preferably has an outer diameter which is just smaller than the inner diameter of lumen 18. Also, piston rod 26 is preferably slidably disposed within lumen 18 such that piston rod 26 can slide in a direction generally parallel to the longitudinal axis of catheter 18, in the direction indicated by arrow 32.

Piston rod 26 is supported for reciprocal movement within lumen 18 by virtue of its outer dimensions relative to the inner dimensions of lumen 18, and also by seal arrangement 34. Seal arrangement 34 is preferably an o-ring type seal which fluidically seals the interior of lumen 18 from the exterior of system 10 through the proximal end of manifold 22. Thus, seal arrangement 34 preferably includes an o-ring 36 which is disposed within a generally annular depression or recess 38 formed in lumen 24 of manifold 22. O-ring 36 is preferably formed of a conventional sealing material, such as silicon rubber, and is secured in annular recess 38 utilizing a suitable adhesive.

The distal end 30 of rod 26, when positioned as shown in FIG. 1, preferably cooperates with the inner periphery of the distal end 14 of catheter 12 to form a bolus chamber 37 for containing a bolus of treatment material. The treatment material contained in chamber 37 can be a drug, growth factors, gene therapy materials, radioactive fluid for restenosis or cancer treatment, clot dissolution agent, or any other desired fluid or liquid material. Also, the material can be injected by high pressure, at high velocity, to mechanically break up clots. As described later in the specification, material delivered by system 10 is administered to a desired site in the body by reciprocation of rod 26 in lumen 18.

The proximal end 28 of piston rod 26 is preferably formed in any suitable manner which allows the user to easily grasp and reciprocate rod 26 within lumen 18. For example, in the above-identified patent applications which are hereby fully incorporated by reference, a number of different proximal grasping and manipulating members are disclosed. In one arrangement, a threadable connection is provided between proximal end 28 of rod 26 and manifold 22. In this way, the user can rotate rod 26 to cause either proximal or distal reciprocal movement within lumen 18. In another preferred embodiment, a release mechanism is provided such that the threadable engagement between rod 26 and manifold 22 can be disengaged to simply push or pull rod 26 for quicker longitudinal movement of rod 26. Then, for finer adjustment of rod 26, the threaded engagement is re-engaged and rod 26 is rotated to accomplish longitudinal movement. Further, in the references which are incorporated herein, various grasping members are provided to facilitate grasping and manipulation of rod 26 by the user. Also, electromechanical (e.g., solenoid) actuation of rod 26 can also be used.

In any case, in a preferred embodiment, catheter 12 is preferably formed of a suitable material to track through desired vasculature and to access a treatment site in the body. Therefore, in operation, prior to being inserted in the vasculature, catheter 12 is preferably filled with a solution, such as saline, such that all areas between rod 26 and the inner wall of lumen 18 are filled with the liquid solution to eliminate any dead space in lumen 18. A therapeutic drug or other fluid material is then loaded into the distal end 14 of catheter 18. This may be done, for example, by moving rod 26 to a position in which its distal end 30 is approximately co-terminus with the opening 20 in lumen 18 of catheter 12. Then, distal end 14 of catheter 12 is placed in the liquid solution to be introduced into the vasculature, and rod 26 is withdrawn a desired distance proximally. Withdrawing rod 26 proximally creates a vacuum in chamber 37 of catheter 12 and thus draws some of the liquid solution to be introduced into chamber 37 of catheter 12. In one preferred embodiment, visual indicia are provided at the proximal end 28 of rod 26 to indicate to the user the total volume of liquid solution which has been drawn into the distal end 14 of catheter 12 based on proximal withdrawal of rod 26.

After catheter 12 has been charged with the treatment solution, distal end 14 of catheter 12 is advanced through the vasculature and positioned proximate a desired treatment site. This can be accomplished in any number of known manners. For example, the distal end 14 of catheter 12 can be provided as a cutting tip which can be used to pierce the skin and enter the desired vessel. Further, a separate cutting device can be provided which is used in conjunction with (e.g., over the top of) catheter 12 to introduce catheter 12 into the desired vessel. Still further, conventional guidewire or guide catheter assemblies can be used in conjunction with catheter 12 to guide catheter 12 to a desired location in the vasculature. Use of a guidewire with catheter 12 is preferably accomplished by either providing a separate lumen in catheter 12, separate from lumen 18, over which catheter 12 can track the guidewire. Alternatively, catheter 12 can be formed as a single-operator-exchange catheter which includes a distal guidewire tube for tracking over the guidewire. Such arrangements are more fully discussed in the above-referenced U.S. patent applications.

In any case, distal end 14 of catheter 12 is advanced under suitable visualization, or according to other positioning techniques, until it resides proximate the site to be treated. Once appropriately positioned, the user advances rod 26 distally such that the distal end 30 of rod 26 creates a positive pressure within chamber 37 of lumen 18 at the distal end 14 of catheter 12. This positive pressure forces the liquid treatment material out the distal opening 20 in catheter 12 so that it is administered at the desired site.

In a preferred embodiment, the volume of the chamber 37, which is defined by the interior periphery of catheter 12 and the distal tip of rod 26, is preferably less than or equal to approximately 1 ml. Thus, it can be seen that the present invention can be used to directly administer a very low volume bolus of drug or other therapeutic material directly to a desired treatment site within the body, using a transluminal technique.

The specific materials used in implementing catheter system 10 can be any suitable, and commercially available materials. For example, manifold 22 is preferably made of an injection molded polycarbonate. Recess 38 within which o-ring 36 resides preferably has approximately a 0.123 inch diameter recess formed in manifold 22, and the inner diameter of lumen 24 in manifold 22 is preferably approximately 0.042 inches. Catheter 12 can be formed of several sections, or only a single section. Catheter 12 can also be made of any suitable materials, depending on the performance characteristics desired. For example, catheter 12 can be made of an extruded polymer tube, stainless steel hypotube, or a composite material such as stainless steel braid encased in polyimide. To impart different characteristics along its length, catheter 12 may incorporate changes in diameter or combine different constructions. For example, catheter 12 may have a composite proximal section combined with a polymer distal section. Other suitable configurations can be used as well.

Rod 26 is preferably made of a stainless steel wire surrounded by a KYNAR™ (polyvinylidene fluoride) tube. The stainless steel wire preferably has a diameter of approximately 0.019 inches and a length of about 50 inches. The tube surrounding the wire preferably has an outside diameter of approximately 0.038 inches and an inside diameter of 0.020 inches. When fully actuated in the distal direction, rod 26 preferably extends such that its distal end 30 is co-terminus with the distal end 14 in catheter 12. Positive stops (not shown) can optionally be provided at the distal end 14 of catheter 12 to limit the distal movement of rod 26.

Generally, connections between the various polymer components may be made utilizing suitable grade medical adhesives or thermal bonds which are well known to those skilled in the art. Connections between metallic components are preferably made, for example, by utilizing solder, by brazing, welding, or other suitable techniques.

FIG. 2 is an enlarged view of a distal end portion 14 of catheter 12. Some items shown in FIG. 2 are similar to those shown in FIG. 1, and are correspondingly numbered. However, FIG. 2 illustrates that, rather than rod 26 simply having distal end 30, a plunger 40 is coupled to distal end 30 of rod 26. Plunger 40 has an outer diameter which is approximately the same as, or just smaller than, the inner diameter of lumen 18. Thus, when rod 26 is actuated in the distal direction, plunger 40 and rod 26 act much like a conventional syringe in that the distal chamber 37 defined by the distal end 14 of catheter 12 and plunger 40, is pressurized. This forces the bolus of treatment material out through the distal opening 20 in catheter 12. However, since plunger 40 is provided, the outer periphery of the remainder of actuating rod 26 need not be approximately the same as, or just smaller than, the interior periphery of lumen 18. Instead, it can be much smaller. This significantly reduces the frictional forces acting on rod 26 as it is reciprocated within lumen 18. It should be noted that plunger 40 can be a separate member attached to the distal end 30 of rod 26, or it can be formed integrally with rod 26 simply by broadening out the distal end 30 of rod 26.

FIG. 3 is another enlarged view of the distal end of rod 26. Some items are similar to those shown in FIG. 2, and are similarly numbered. However, rather than simply having plunger 40, the embodiment shown in FIG. 3 includes plunger head 42. Plunger head 42 includes a pair of discs 44 and 46 which are mounted about the outer periphery of the distal end 30 of rod 26. The discs 44 and 46 are preferably separated by an o-ring 48 formed of silicone or other suitable material and sized to fluidically seal lumen 18. Discs 44 and 46 are also preferably formed of silicon rubber material, or other suitable material, or can be formed integrally with rod 26.

FIG. 4 is an enlarged side sectional view of the distal end 14 of catheter 12 in accordance with another aspect of the present invention. Some items are similar to those shown in FIG. 2 and are correspondingly numbered. However, rather than simply having a distal opening 20 in the distal end 14 of catheter 12, FIG. 4 illustrates that a separable seal 50 is provided in distal end 14. Separable seal 50 preferably includes a rubber or polymer material inserted into the distal end 14 of catheter 12 and connected thereto with a suitable adhesive.

Separable seal 50 preferably includes a seam 52 therein. Seam 52 is simply formed by the abutment of the surfaces of seal 50 against one another, but those portions are not adhesively or otherwise sealed to one another (other than through friction). This arrangement allows the introduction of a conventional, small diameter, needle which is attached to a syringe containing the treatment solution into the distal end 14 (and hence chamber 37) of catheter 12, and through seam 52. Thus, the treatment solution can be injected into chamber 37 of catheter 12, as plunger 40 is withdrawn in the proximal direction to draw the treatment solution therein.

Once the distal end 14 of catheter 12 is placed at the treatment site in the vasculature, distal actuation of rod 26 causes plunger 40 to create a pressure behind seal 50 causing seal 50 to separate at seam 52 and thus release the treatment solution at the desired location. In another preferred embodiment, seal 50 is a rolling diaphragm type of seal, or another suitable type of seal configuration.

FIG. 5 is an enlarged side sectional view of distal end 14 of catheter 12 in accordance with another aspect of the present invention. Similar items are similarly numbered to those shown in previous figures. However, FIG. 5 illustrates that the distal tip of catheter 12 is provided with a needle having a plurality of apertures 54 therein. Apertures 54 allow the treatment solution 37 to be withdrawn into the distal end 14 of catheter 12, and to be forced out through the distal end thereof.

FIG. 6 illustrates yet another embodiment in accordance with the present invention. FIG. 6 is similar to FIG. 5 except that, rather than having uniformly spaced apertures 54 at the distal tip of catheter 12, the distal tip or nozzle region is provided with side ports 56 which allow the treatment solution in chamber 37 to be directionally administered in the direction in which side ports 56 are disposed.

FIG. 7 illustrates another preferred embodiment in accordance with the present invention. Similar items are similarly numbered to those shown in previous figures. However, the distal end of catheter 12, rather than being provided as a solid member with apertures therein, is provided as a porous needle portion 58. Porous needle portion 58 can be provided as a microporous membrane, as a selectively porous membrane, or as any other suitable porous or capillary type material, suitable for the introduction of treatment solution from chamber 37 to the treatment site.

FIG. 8 is a side sectional view of a catheter system 60 in accordance with another preferred embodiment of the present invention. Some items are similar to those shown in FIGS. 1-7, and are similarly numbered. However, catheter 12 is also provided with a treatment fluid reservoir 62 defined by wall 64 which is preferably arranged about an exterior portion of catheter 12. Reservoir 62 extends from a distal end 66 which is arranged just proximal of administration tip (or nozzle) 68, to a proximal end 70 which is provided with a suitable fitting for receiving the treatment solution.

In operation, the treatment solution is preferably injected, using a standard syringe, through proximal portion 70 of reservoir 62. A flapper valve 72 is preferably provided at distal end 66 of reservoir 62 to fluidically separate lumen 18 in catheter 12 from reservoir 62. In the preferred embodiment, flapper valve 72 is arranged such that it pivots generally in a direction indicated by arrow 74 and is hingedly attached by hinge 76 to the wall of catheter 12. Flapper valve 72 has a distal end 78 which engages a positive stop 80 on the inside of lumen 18 of catheter 12.

Therefore, when plunger 40 is withdrawn proximally, this creates a vacuum or low pressure area within chamber 37, relative to reservoir 62. This causes flapper valve 72 to lift upwardly to allow fluid to escape from reservoir 62 into chamber 37. Then, when plunger 40 is advanced distally, this creates a high pressure region in lumen 18 relative to reservoir 62 so that flapper valve 72 closes and the distal end 78 of flapper valve 72 abuts positive stop 80.

As plunger 40 continues to be advanced distally, the treatment solution in chamber 37 is passed through administering tip 68 to the desired site. In the preferred embodiment, administering tip 68 is provided with very small apertures, or pores, or valved openings, such that a greater pressure differential is required between the interior lumen 18 and the exterior of catheter 12 to cause liquid material to pass through administering tip 68 than is required to lift flapper valve 72. Therefore, as plunger 40 is withdrawn proximally, flapper valve 72 opens to allow the treatment material in chamber 62 to enter lumen 18, but no fluid, or very little fluid, is drawn into lumen 18 from outside catheter 12. Then, as plunger 40 is advanced distally, flapper valve 72 closes and a great enough pressure is built within chamber 37 to cause the treatment material to pass through administering tip 68 to the desired position.

It will thus be appreciated that the embodiment disclosed in FIG. 8 allows the user to position distal tip 14 of catheter 12 at the desired location within the body before chamber 37 is charged with the bolus of treatment material to be injected at the treatment site.

FIG. 9 shows another embodiment of the distal end 14 of catheter 12 in catheter system 60. Similar items are similarly numbered to those shown in FIG. 8. However, rather than providing reservoir 62 extending all the way from distal end 66 thereof to proximal end 70 thereof, reservoir 62 is maintained only at a distal portion of catheter 12. Reservoir 62 is also provided with a suitable introduction valve 82 which can preferably be used in conjunction with a conventional syringe, to introduce the bolus of treatment material into reservoir 62. By not requiring reservoir 62 to extend all the way to the proximal end 70, the internal volume of reservoir 62 can be kept very small. This facilitates utilizing only a needed volume of treatment material. No extra material is required to fill the internal volume of reservoir 62, since that volume is so small.

FIG. 10 shows another preferred embodiment of the catheter system 84 in accordance with the present invention. Catheter system 84 is similar to catheter system 60 shown in FIG. 8, and similar items are similarly numbered. However, catheter system 84 includes a modified form of treatment reservoir 62. Rather than terminating in its proximal area at proximal end 70, the proximal end of reservoir 62 in catheter system 84 extends all the way through proximal manifold 22 in the same fashion as lumen 24. Also, reservoir 62 is provided with a reciprocally mounted rod 86 and plunger 88. Further, rod 86 is sealably mounted within manifold 22 by seal configuration 90 which is similar to seal configuration 34 discussed with respect to FIG. 1. The proximal ends of rods 26 and 86 can optionally be either connected to one another, or separate from one another for separate actuation by the user.

In any case in order to introduce the bolus of treatment material into reservoir 62, rod 86 and plunger 88 are advanced to the distal most actuation point in which they abut a second flapper valve arrangement 92. Flapper valve 92 is biased to normally close an aperture 94 against an inner portion 96 of the distal end of reservoir 62. Then, the distal tip 14 of catheter 12 and reservoir 62 are placed in the drug solution to be administered. Rod 86 and plunger 88 are then withdrawn distally a desired amount such that flapper valve 92 opens to allow the fluid to be administered to enter reservoir 62 through aperture 94. When the distal tip 14 of catheter 12 is appropriately positioned in the vasculature, rod 86 and plunger 88 are then advanced distally to charge catheter 12 by introducing the material to be administered from reservoir 62, through flapper valve arrangement 72, and into chamber 37 in catheter 12. Once charged, catheter 12 is ready to administer the treatment solution. Thus, the user advances rod 26 and plunger 40 such that the bolus of treatment solution is injected from chamber 37 through the administering tip of catheter 12 to the desired site.

FIG. 11 shows another catheter system 98 in accordance with another preferred embodiment of the present invention. Similar items are similarly numbered to those shown in previous figures. Catheter system 98 is similar to catheter system 84 and similar items are correspondingly numbered. However, rather than providing two rods 26 and 86, as in FIG. 10, catheter system 98 includes bifurcated rod 100. Bifurcated rod 100 includes first leg portion 102 which is connected to plunger 40 and which resides within lumen 18 of catheter 12. Bifurcated rod 100 also includes second leg portion 104 which is connected to plunger 88 and lies in reservoir 62. Catheter system 98 shown in FIG. 11 is also preferably provided with a valve arrangement similar to valve arrangement 82 shown in FIG. 9 by which the treatment material is inserted into reservoir 62.

In the embodiment shown in FIG. 11, the treatment material is simultaneously introduced from reservoir 62 into chamber 37 distal of plunger 40, and the bolus of material is injected at the desired site, as the user advances bifurcated rod 100 distally. Plunger 82 causes high pressure in reservoir 62 to move the bolus of treatment material from reservoir 62 into chamber 37 distal of plunger 40. At the same time, plunger 40 causes high pressure to be developed in chamber 37 such that the bolus of material is advanced through the administering tip to the desired site.

FIG. 12 is similar to FIGS. 10 and 11, and similar items are similarly numbered. However, reservoir 62 is provided with different valve arrangements. Rather than flapper valve 72, a simple aperture 106 is provided between reservoir 62 and lumen 18. A plunger 108 is sized to completely cover aperture 106 when it is advanced to its distal most position (shown in phantom in FIG. 12). Thus, the operator can advance plunger 108 within reservoir 62 to charge lumen 18 with a bolus of material. The operator can, either simultaneously or separately, advance plunger 40 to administer the material through the tip of the catheter, once chamber 37 has been charged with the bolus.

FIG. 13A is a side sectional view of catheter 120 in accordance with another embodiment of the present invention. Catheter 120 includes proximal manifold 122, shaft portion 124 and distal end 126. Shaft portion 124 includes inflation lumen 128, guidewire lumen 130 and infusion lumen 132. Shaft portion 124 also includes a wall or sealing portion 134 at its distal end which is sealably connected to the inner portion of the outer sheath forming shaft portion 124, and also to the outer perimeter of guidewire lumen 130 and infusion lumen 132. Wall 134 also preferably has an inflation tube 136 disposed therein which provides fluid communication between inflation lumen 128 and the interior of balloon 138 on distal portion 126.

Distal portion 126 includes inner balloon 138 and outer membrane 140 and is configured such that guidewire lumen 130 extends therethrough to a distal portion 142 thereof. Balloon 138, in one preferred embodiment, is a conventional dilatation balloon which is bonded at a first bond location 144 to the sheath forming tubular portion 124, and at a second bond location 146 to the outer periphery of guidewire lumen 130.

Figure 14C:
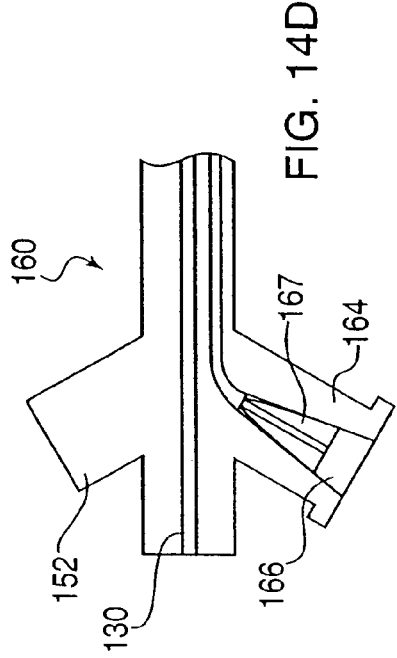

In another preferred embodiment, balloon 138 is formed as a channel balloon structure 300 as shown in FIG. 13B. Channel balloon structure 300 may be used in place of the combination of balloon 138 and outer membrane 140 as illustrated in FIG. 13A. The low volume drug delivery aspects discussed with reference to catheter 120 may be adapted for use with channel balloon structure 300. In particular, the modified syringe discussed with reference to FIGS. 14A-14C are preferably suitable for use with, but not limited to, the channel balloon structure 300.

Figure 13D:
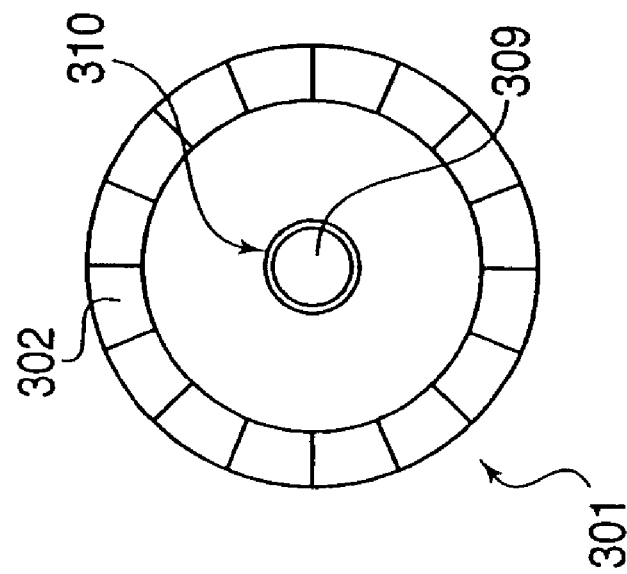
FIG. 13D is a cross-sectional view taken along line D-D in FIG. 13B.

The channel balloon structure 300 includes a channel balloon 301 having a plurality of longitudinal channels 302 as best seen in FIG. 13D. The longitudinal channels 302 are in fluid communication with the infusion lumen 303 shown in FIG. 13C. A fluid connection between the infusion lumen 303 and the longitudinal channels 302 is provided by infusion port 304 and connection tube 305. Channel balloon 301 also includes a plurality of infusion holes 306 which provide fluid communication between the longitudinal channels 302 and the exterior of the balloon 301. Accordingly, fluid may be delivered via the infusion lumen 303 out the infusion port 304 through the connection tube 305 and into the longitudinal channels 302 of the channel balloon 301. The fluid then passes from the channels 302 out the infusion holes 306 to the desired treatment site.

Figure 13C:
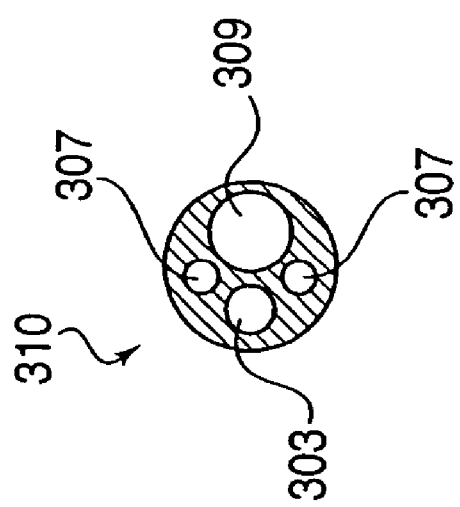
FIG. 13C is a cross-sectional view taken along line C-C in FIG. 13B.

The channel balloon 301 may be inflated by introducing pressurized inflation media through inflation lumens 307 as best seen in FIG. 13C. Inflation lumens 307 communicate with the interior of the balloon 301 by inflation ports 308. As such, the channel balloon 301 may be inflated independently of the delivery of fluid to the treatment site. The channel balloon structure 300 may also include a guidewire lumen 309 for advancing the catheter over a conventional guidewire.

The channel balloon 301 may be connected to the shaft 310 using conventional adhesives or thermal bonding techniques. In a similar manner, the connection tube 305 may be connected to the outside of the proximal end of the channel balloon 301 and to the shaft 310 using similar techniques. The shaft 310 is preferably necked-down immediately distal of the inflation ports 308. In this manner, the channel balloon 301 may be wrapped about the shaft 310 to form a low profile folded balloon capable of traversing relatively tight vascular restrictions. These and other aspects of the channel balloon structure are more fully disclosed in PCT publication No. WO 98/10824 to Lin et al., which is hereby incorporated fully by reference.

Referring back to FIG. 13A, outer membrane 140 can also be formed in any number of suitable ways. For example, outer membrane 140 can simply be a microporous membrane which is expandable with the expansion of balloon 138. Outer membrane 140 can also be formed of conventional balloon material, having a plurality of apertures 150 formed therein for infusion of the bolus of treatment solution. Of course, as described above with respect to FIG. 6, apertures 150 can be disposed about the entire periphery of outer membrane 140, or they can be disposed only in one portion of outer membrane 140 to accomplish directional infusion.

Proximal manifold 122 includes inflation port 152 and infusion port 154. Inflation port 152 is coupled to shaft portion 124 such that it is in fluid communication with inflation lumen 128 and also (through inflation tube 136) with the interior of balloon 138. Inflation port 152 is preferably formed in a known manner such that the application of pressurized fluid through inflation port 152 pressurizes inflation lumen 128 to drive inflation of balloon 138. Infusion port 154 is preferably provided with a very small diameter tube 156 which is in fluid communication with infusion lumen 132.

In order to infuse the bolus of treatment solution, the distal end 126 of catheter 120 is first positioned proximate the site to be treated with a treatment solution. Balloon 138, and consequently membrane 140, are in a deflated, low profile position. Catheter 120 is advanced through the vasculature to the treatment site. The treatment solution is then injected through tube 156 into infusion lumen 132 using a conventional syringe, or a modified syringe discussed below with respect to FIGS. 14A-14D, such that the treatment solution exits infusion lumen 132 into chamber 158 which is defined by the inner surface of membrane 140 and the outer surface of balloon 138. Balloon 138 is then inflated in order to force the treatment solution through membrane 140 to the desired treatment site. In a preferred embodiment, balloon 138 is formed such that in the inflated position it closely conforms to the inner periphery of membrane 140.

The dead space of an infusion system, when discussed in accordance with the present invention, refers to the volume remaining in the infusion system once infusion is complete. Thus, after infusion, the dead space in the system typically contains additional, unused infusate. In accordance with one aspect of the present invention, infusion tube 156, infusion lumen 132, and the portion of chamber 158 which remains open after complete inflation of balloon 138, all together, define a dead space of less than approximately 0.32 cubic centimeters (cc) and preferably less than 0.15 cc. In a preferred embodiment, the infusion tube 156 and proximal manifold 122 have no more than approximately 0.02 cc dead space, and infusion lumen 132 and the dead space in chamber 158, together, comprise less than approximately 0.13 cc. If the channel balloon structure 300 is utilized, the infusion lumen 132 and the dead space in connection tube 305 and channels 302, together, comprise less than approximately 0.16 cc. Table 1 provides examples of suitable parameters for the manifold, the infusion lumen, and the delivery mechanism (e.g., balloon structure) with resulting total dead space for a coronary drug delivery catheter of the present invention.

TABLE 1

| DEVICE | MANIFOLD DEAD SPACE (CC) | INFUSION LUMEN DEAD SPACE (CC) | DELIVERY MECHANISM DEAD SPACE (CC) | TOTAL DEAD SPACE (CC) |
| --- | --- | --- | --- | --- |
| PRIOR ART #1 | 0.20 | 0.52 | 0.00 | 0.72 |
| PRIOR ART #2 | 0.20 | 0.43 | 0.02 | 0.65 |
| PRIOR ART #3 | 0.20 | 0.24 | 0.01 | 0.45 |
| INVENTION #1 | 0.04 | 0.23 | 0.05 | 0.32 |
| INVENTION #2 | 0.03 | 0.17 | 0.03 | 0.23 |
| INVENTION #3 | 0.02 | 0.11 | 0.02 | 0.15 |
| INVENTION #4 | 0.01 | 0.06 | 0.01 | 0.08 |
| INVENTION #5 | 0.00 | 0.00 | 0.00 | 0.00 |

As can be seen from Table 1, the total densities for known prior art drug delivery catheters for coronary application ranges from 0.45 to 0.72 cc. By contrast, the total dead space for a coronary drug delivery catheter of the present invention ranges from 0.00 to 0.32 cc. It is contemplated that the manifold dead space of the present invention may be approximately 0.00 cc if a manifold was eliminated from the catheter. It is possible to eliminate the manifold from the drug delivery catheter I, for example, utilizing one of the embodiments illustrated in FIGS. 18A-18H. In a similar manner, it is also contemplated that the infusion lumen dead space may be approximately 0.00 cc if a coronary drug delivery catheter of the present invention was to incorporate one of the embodiments illustrated in FIGS. 18A-18H. The delivery mechanism of the present invention may also be approximately 0.00 cc if an open-ended lumen is utilized as a delivery mechanism. As mentioned herein, the delivery mechanism may comprise a balloon structure, a needle, an open-ended lumen or any other suitable structure capable of delivering the therapeutic fluid to the treatment site.

FIGS. 14A-14D illustrate a proximal manifold and syringe in accordance with another aspect of the present invention. FIG. 14A illustrates a proximal manifold 160 and infusion syringe 162. Proximal manifold 160 is shown with an inflation port 152, a guidewire lumen 130, and an infusion port 164. Infusion port 164 has a syringe receiving chamber 166 which is coupled to infusion tube 156. Infusion tube 156, as discussed with respect to FIG. 13, is preferably in fluid communication with infusion lumen 132.

Between syringe receiving chamber 166 and infusion tube 156, proximal manifold 160 preferably has a self-sealing member 168. Self-sealing member 168, in one preferred embodiment, is a rubber seal which is coupled, through adhesive or other suitable means, to shoulder 170 of syringe receiving chamber 166. Shoulder 170 is disposed, at a distal region of syringe receiving chamber 166 where syringe receiving chamber 166 comes into fluid communication with infusion tube 156.

Figure 14D:
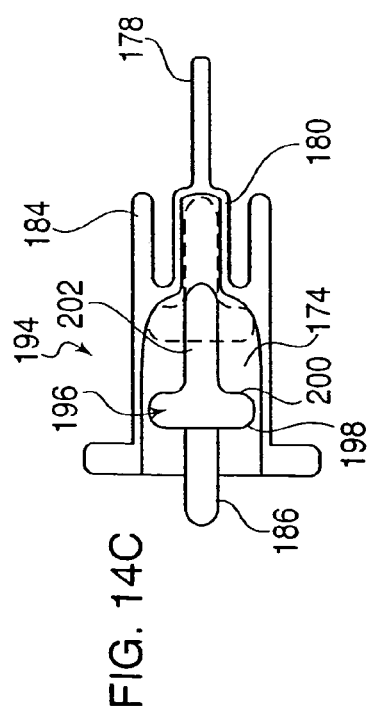

Alternatively (as shown in FIG. 14D), member 168 can be replaced by a molded insert 167 which is molded integrally or separately from proximal manifold 160. Insert 167 is then placed in infusion port 164 and bonded or otherwise secured therein. Insert 167 thus reduces dead space in infusion port 164 of proximal manifold 160, while facilitating use of a conventional infusion syringe (such as a syringe without a needle).

Referring again to FIG. 14A, syringe 162 includes plunger 172 which is disposed within an inner chamber 174 of barrel portion 176. Chamber 174 is tapered, or otherwise conformed to achieve a reduced interior radius, at its distal end. Syringe 162 also includes needle 178 which defines a lumen therein in fluid communication with chamber 174. Needle 178 is coupled to an annular collar 180 through a coupling member 182. Needle 178 is preferably a molded tube formed of the same material as the barrel of syringe 162, or a hypotube (such as a tube made of Nitinol, stainless steel or other suitable material) which is bonded within collar 180 in syringe 162. Coupling member 182, in one preferred embodiment, is simply a suitable adhesive, but can also be a rubber silicone sealing gasket, or other suitable sealing member. Needle 178 is sized to advance through self-sealing member 168 and nest within infusion tube 156. Annular collar 180 is sized to snugly fit within syringe receiving chamber 166 in proximal manifold 160. Syringe 162 also includes outer annular collar 184. Collar 184 preferably includes threads to screw onto infusion port 164 or has an inner periphery which is sized just larger than the outer periphery of infusion port 164 to snugly fit about the outer periphery of infusion port 164.

Plunger 172, in one preferred embodiment, includes shaft 186 and piston 188. Shaft 186 is preferably rigidly coupled to piston 188. Piston 188 has an enlarged outer diameter portion 190 which is sized to snugly fit within chamber 174, and is slidably disposed within chamber 174. Piston 188 also has a distal end 192 which is shaped such that it closely conforms to the inner taper of barrel 174. Therefore, when rod 186 is advanced within chamber 174, distal end 192 of piston 188 advances until it contacts the proximal end of needle 178. In that position, the outer conformation of piston 188 preferably closely conforms to the inner conformation of barrel 174 to eliminate substantially all dead space from barrel 174.

In operation, the catheter coupled to proximal manifold 160 is preferably placed within the vasculature such that its distal end is at the desired treatment site. Syringe 162 is charged with treatment liquid by placing the distal end of needle 178 in the treatment liquid and withdrawing plunger 172 to draw treatment solution into barrel 174 between the distal end 192 of piston 188 and the distal end of needle 178. Syringe 162 is then connected to infusion port 164 as shown in FIG. 14B.

FIG. 14B illustrates that collar 184 preferably fits snugly about the exterior periphery of infusion port 164. Also, collar 180 fits snugly within syringe receiving chamber 166 in infusion port 164. Needle 178 is preferably sized such that its distal end pierces self-sealing member 168 and enters within infusion tube 156. As illustrated in FIG. 14B, the exterior periphery of needle 178 preferably includes threads thereon to screw into infusion tube 156 or snugly fits (such as through a slip fit or a light frictional fit) within the inner periphery of infusion tube 156. Plunger 172 is then advanced such that its distal end 192 nests closely proximate the proximal end of needle 178. Thus, the treatment solution in chamber 174 is forced out through needle 178 into infusion tube 156. It can thus be seen that substantially the only dead space associated with syringe 162 is that within the interior of needle 178. Substantially the only dead space in proximal manifold 160 and syringe 162 is that within needle 178 and within the interior of infusion tube 156 distal of the distal end of needle 178.

FIG. 14C illustrates another embodiment of a syringe 194 in accordance with another aspect of the present invention. Syringe 194 has some items which are similar to those shown in FIGS. 14A and 14B with respect to syringe 162, and those items are similarly numbered. However, rather than having a separate needle 178 disposed within annular collar 180, annular collar 180, itself, acts as the needle. In other words, annular collar 180 is dimensioned such that it pierces self-sealing member 168 shown in FIG. 14A when syringe 194 is connected to proximal manifold 160. Also, syringe 194 includes piston 196. Piston 196 has a proximal annular portion 198 which has an outer periphery sized to snugly fit within barrel 174. Annular portion 198 also has a distal surface 200 which has a conformation which closely matches the inner conformation of barrel 174 at its distal end.

Piston 196 also has a distal protrusion 202 which has an outer periphery sized to snugly fit within the interior of annular collar 180, and a length which is preferably sufficient such that the distal tip of protrusion 202 is approximately co-terminus with the distal end of collar 180 when piston 196 is advanced all the way to the distal end of barrel 174. Piston 196 is shown advanced to such a position in phantom in FIG. 14C.

In this way, as piston 196 is advanced distally within syringe 194, annular portion 198 closely conforms to the interior periphery of barrel 174 to eliminate dead space in barrel 174. Protrusion 202 extends all the way through the inner periphery of annular collar 180, and closely conforms thereto, to eliminate the dead space within annular collar 180. Thus, syringe 194 has substantially no internal dead space associated therewith.

In another preferred embodiment, needle 178 is attached to the distal most end of annular collar 180. Thus, the only dead spaced associated with that embodiment of syringe 194 is the dead space located within needle 178 distal of the distal most end of annular collar 180. Thus, protrusion 202 substantially eliminates additional dead space which is associated with needle 178 in the embodiment in which needle 178 extends proximally within annular collar 180.

In one preferred embodiment, needle 178 and infusion tube 156 are dimensioned such that the entire dead spaced associated with proximal manifold 160 and either syringe 162 or syringe 194 is less than approximately 0.002 cc, and even more preferably less than approximately 0.001 cc.

Figure 15A:
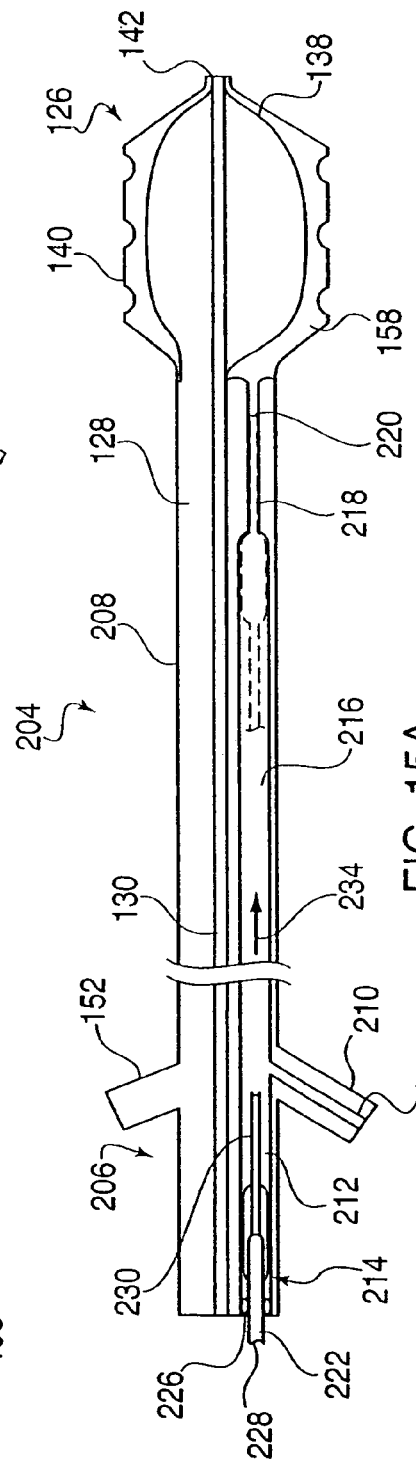
FIGS. 15A and 15B illustrate a side sectional view of a catheter, and a side view of a piston, respectively, in accordance with one aspect of the present invention.

FIG. 15A is a side sectional view of a catheter 204 in accordance with another aspect of the present invention. A number of the items in catheter 204 are similar to those shown in FIG. 13 with respect to catheter 120, and are similarly numbered. Catheter 204 includes proximal manifold 206, shaft portion 208, and distal portion 126. Proximal manifold 206 includes inflation port 152, infusion port 210, and infusion lumen 212. Catheter 204 also includes piston 214 slidably disposed within infusion lumen 212.

Shaft portion 208 includes an outer sheath defining inflation lumen 128, and having guidewire lumen 130 extending therethrough. Shaft portion 208 also includes infusion lumen 216 which is in fluid communication with infusion lumen 212 and proximal manifold 206. Infusion lumen 216 terminates, at its distal end, in a small diameter connection lumen 218, which connects the interior of infusion lumen 216, with chamber 158 in distal tip 126 of catheter 204.

Lumen 218, in one preferred embodiment, has a pressure valve 220 disposed at its distal end. In an illustrative embodiment, pressure valve 220 is simply formed as a piece of rubber or silicon adhered within lumen 218 and having a slit therein. When pressure on the proximal end of valve 220 is greater, by some desired threshold, than the pressure on its distal end, the slit or seam opens to allow fluid communication between lumen 218 and chamber 158.

Piston 214 preferably includes shaft 222 which has an outer periphery sized to sealably engage a sealing member 226 disposed at the proximal end of infusion lumen 212. Shaft 222 is also preferably in slidable engagement with sealing member 226. Piston 214 preferably has an outer periphery which is sized to snugly and slidably fit within the interior of infusion lumens 212 and 216. In one preferred embodiment, shaft 222 includes a proximal shaft portion 228 and a smaller diameter distal shaft portion 230. Proximal shaft portion 228 is preferably formed as a Nitinol or stainless steel wire, while distal shaft portion 230 is preferably formed of a small diameter Nitinol wire. Alternatively, shaft 222 can be formed of a single piece of material having a single outer diameter extending the entire length thereof, or having a tapered section which tapers to a smaller diameter between a proximal region of shaft 228 and the distal region of shaft 230.

In operation, piston 214 is preferably first withdrawn proximally such that the distal end of piston 214 is just proximal of, or aligned with, infusion tube 232 in infusion port 210. A vacuum is then pulled through infusion port 210. The bolus of treatment solution to be administered is then injected through infusion tube 232 using a conventional syringe, or using one of syringes 162 and 194 described with respect to FIGS. 14A-14C above, or another suitable charging device. Piston 214 is then advanced using proximal shaft portion 222 such that piston 214 has its proximal end just distal of infusion tube 232.

Infusion port 210 is then coupled to a source of pressurized fluid, such as to a syringe containing contrast medium, saline solution, or another suitable fluid. Fluid under pressure is then injected through infusion port 210 at a high enough pressure to drive piston 214 distally, in the direction indicated by arrow 234. The piston 214 slides distally, in tight engagement with the inner walls of infusion lumen 216 driving the bolus of therapeutic solution distally. Piston 214 is driven further distally until distal shaft portion 230 engages, and moves within, small diameter lumen 218 at the distal end of infusion lumen 216.

In a preferred embodiment, distal shaft portion 230 has an outer periphery sized to snugly, and slidably, fit within reduced diameter lumen 218. Distal shaft portion 230 is also preferably formed to have a length sufficient to reach to an area within lumen 218 adjacent, or just proximal of, valve 220. Also, the distal end of piston 214 has an outer conformation which closely conforms to the inner conformation of the distal end of infusion lumen 216. Thus, as piston 214 is driven to its furthest distal position (shown in phantom in FIG. 15A) substantially all of the bolus of treatment solution is driven from infusion lumen 216, through lumen 218 and through, pressure valve 220 into chamber 158, and through membrane 140 to the treatment site. Alternatively, if the channel balloon structure 300 is utilized as depicted in FIG. 13B, substantially all of the bolus of treatment solution is driven into the longitudinal channels 302, out the infusion holes 306 and to the treatment site. It can thus be seen that catheter 204 eliminates all dead space therein, other than a very small amount of dead space in the balloon.

Figure 15B:
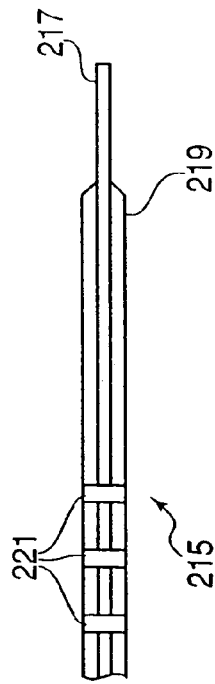

FIG. 15B illustrates another embodiment of a piston 215 for use with catheter 204. Piston 215 includes wire 217 which is preferably a Nitinol core wire. Piston 215 also includes a plastic overcoat 219 which is coated over a proximal region of wire 217. Plastic overcoat 219 preferably has an outer diameter which snugly, and slidably, fits through seal 226 and fits within infusion lumens 212 and 216. Plastic overcoat 219 is preferably provided, at its proximal end, with a number of indicia 221 which are used by the operator to determine a volume of infusate which has been administered with catheter 204. Overcoat 219 is illustratively formed of a plastic or other suitable material which reduces frictional forces encountered in advancing piston 215.

In operation, piston 215 is withdrawn such that the distal end of plastic overcoat 219 is located just proximal of infusion tube 232. A vacuum is then pulled through infusion tube 232, and the bolus of treatment solution is inserted through infusion tube 232 into infusion lumen 212. The infusion port 210 is then closed. Piston 215 is then advanced distally by the operator to move the bolus of treatment solution distally within infusion lumen 216. As piston 215 is advance distally, pressure in infusion lumen 216 builds to the actuation point of valve 220. This causes valve 220 to open to allow the bolus of treatment solution to be advanced through lumen 218 into chamber 158 where it is dispensed. As with the previous embodiment, the dimension of Nitinol wire 217 is sized to fit snugly within lumen 218 such that the distal end of wire 217, when piston 215 is advanced all the way distally, resides just proximal of valve 220. In addition, the distal end of plastic overcoat 219 has an outer conformation which closely matches the inner conformation of the distal end of infusion lumen 216 in order to eliminate dead space.

FIGS. 16A-16D illustrate a catheter 240 in accordance with another aspect of the present invention. Some items associated with catheter 240 are similar to those described with respect to embodiments shown in earlier figures, and are similarly numbered.

Catheter 240 includes proximal manifold 242, shaft portion 244 and distal portion 126. Proximal manifold 242 includes inflation port 152 and infusion port 246. Infusion port 246 includes infusion tube 248 therein. Shaft portion 244 includes inflation lumen 128, guidewire lumen 130 and collapsible fluid reservoir 250. Collapsible fluid reservoir 250 is preferably formed of a pliable material, such as conventional balloon material, or other suitable material, and has a proximal end 252 which is coupled to infusion tube 248 and is in fluid communication therewith. Reservoir 250 also has a distal end 254 which is coupled to, and in fluid communication with, reduced diameter lumen 218 which also illustratively includes pressure valve 220. Reservoir 250 is preferably disposed within inflation lumen 128.

In operation, either before or after distal end 126 of catheter 240 is placed adjacent the treatment site in the vasculature, a suitable mechanism, such as a syringe, is coupled to infusion port 246 and infusion tube 248. A vacuum is pulled on infusion port 246 to collapse reservoir 250. A cross-section of catheter 240, taken along section lines 16-16 in FIG. 16A is illustrated in FIG. 16D. FIG. 16D illustrates reservoir 250 in the collapsed position.

After reservoir 250 is collapsed, treatment solution is injected into reservoir 250 through infusion port 246. Infusion port 246 is then closed. FIG. 16C illustrates the same cross-section of catheter 240 shown in FIG. 16D, except with reservoir 250 in the expanded position containing infusate.

After balloon 132 of catheter 240 is placed at the treatment site, pressurized fluid is injected through inflation port 152 into inflation lumen 128. As balloon 138 inflates, pressurized fluid is continually injected into inflation lumen 128 to build pressure in inflation lumen 128. As the pressure in inflation lumen 128 builds, it exerts a pressure on collapsible reservoir 250 tending to collapse reservoir 250. Thus, the pressure within reservoir 250 gradually increases to the actuation point of valve 220. At that point, valve 220 opens and reservoir 250 collapses under the pressure in inflation lumen 128 thus forcing the infusate from reservoir 250 through lumen 218 and valve 220 into chamber 158. The infusate then exits through membrane 140 in the manner described above.

FIG. 16B is a cross-sectional view of catheter 240 with reservoir 250 in the collapsed position. It should be noted that, under sufficient pressure, reservoir 250 substantially entirely collapses leaving no dead space within reservoir 250. This significantly reduces the dead spaced associated with catheter 240, without the requirement of a moving plunger, or another movable piston element within reservoir 250.

FIGS. 17A-17D illustrate a catheter 260 in accordance with another preferred embodiment of the present invention. Some items of catheter 260 are similar to those in previous embodiments, and are similarly numbered.

Catheter 260 includes proximal manifold 262 and shaft portion 264, as well as distal portion 126. Proximal manifold 262 includes inflation port 152 which is in fluid communication with inflation lumen 128 which is used for introducing pressurized fluid into balloon 138 to inflate balloon 138. Proximal manifold 262 also includes infusion ports 266 and 268. Infusion port 268 includes infusion tube 270 which has a distal end connected to, and in fluid communication with, collapsible reservoir 272 in shaft portion 264 of catheter 260. Port 268 has an infusion tube 274 which is in fluid communication with pressure lumen 276 in shaft portion 264 of catheter 260.

Operation of catheter 260 is similar to that of catheter 240 shown in FIG. 16A. However, rather than having collapsible reservoir 272 being collapsed by inflation pressure for inflating balloon 138, collapsible reservoir 272 is collapsed by a separate pressurized fluid introduced through port 268 and infusion tube 274. Thus, during operation, a vacuum is first pulled through infusion port 266 to collapse reservoir 272. The treatment solution is then injected through infusion tube 270 into reservoir 272 and port 266 is closed. Pressurized fluid is then introduced through infusion tube 274 in port 268. The pressurized fluid is introduced into lumen 276 surrounding collapsible reservoir 272. As the pressure builds in lumen 276, the pressure outside reservoir 272 tends to collapse reservoir 272 and thus increase the pressure on the inside of reservoir 272. As the interior pressure in reservoir 272 increases to the actuation point of valve 220, valve 220 opens thus allowing reservoir 272 to completely collapse and displace the treatment solution therein through lumen 218 and valve 220 into chamber 158, where it is administered through membrane 140.

As with collapsible reservoir 250 in FIG. 16A, collapsible reservoir 272 is preferably formed of conventional balloon material and is bonded at its proximal end to the distal end of infusion tube 270 and at its distal end to the proximal end of lumen 218. The overall length of collapsible reservoir 272 is preferably approximately 80 cm with an interior inflated diameter of approximately 0.022 inches, thus giving rise to a volume in reservoir 272 of approximately 0.2 cc. The total dead space for catheter 260, including proximal manifold 262, is thus preferably approximately 0.06-0.1 cc.

FIG. 17B illustrates catheter 260 with reservoir 272 in the collapsed position. It can be seen that, as pressure builds with the injection of pressurized fluid into lumen 276, collapsible reservoir 272 substantially completely collapses leaving no dead space therein.

FIGS. 17C and 17D illustrate cross-sections of catheter 260 in an alternate embodiment of catheter 260. In FIGS. 17C and 17D, collapsible reservoir 272 and lumen 276 are formed externally to inflation lumen 128. The wall defining lumen 276 is also preferably formed of a collapsible material, such as conventional balloon material. FIG. 17C illustrates lumen 276 and reservoir 272 in an insertion position in which the distal end of catheter 260 is inserted into the vasculature. Since both lumen 276 and reservoir 272 are collapsible, they are preferably introduced into the vasculature in the collapsed, low profile position which facilitates manipulation of catheter 260 in the vasculature. FIG. 17D illustrates both lumen 276 and reservoir 272 in the inflated, higher profile position. In the preferred embodiment, lumen 276 and reservoir 272 are only inflated once catheter 260 is in place with distal end 126 at the treatment site. Reservoir 272 and lumen 276 are then again collapsed by pulling vacuums thereon, during removal of catheter 260.

Refer now to FIGS. 18A-18H which illustrate yet another embodiment of the present invention utilizing a collapsible membrane. FIGS. 18A-18H are schematic illustrations only and do not define the specific structure in which the concepts may be employed. It is contemplated that the concepts embodied in FIGS. 18A-18H may be employed in a wide variety of drug delivery catheters such as those illustrated in FIGS. 16A and 17A.

Refer now to FIG. 18A which illustrates a generic catheter shaft 401 having a proximal end connected to a pressure/vacuum source 402 and a distal end connected to a delivery mechanism 403. The catheter shaft 401 preferably has a structure similar to the catheter shafts disclosed in the present application. The pressure/vacuum source 402 may be in the form of a conventional syringe or other suitable alternative. Delivery mechanism 403 may be in the form of a porous balloon, a channel balloon, a puncturing member (e.g., needle), an open-ended lumen or other suitable mechanism for administering a drug to a specific treatment site.

Catheter shaft 401 includes a rigid outer member 404 and a collapsible inner member 405. The collapsible inner member 405 contains the desired drug for administration to the treatment site. Pressure source 402 delivers a desired pressure P1 to the space between the outer membrane 404 and the inner membrane 405. The inner membrane 405 contains a low volume of fluid at pressure P2. When pressure source 402 is maintained at ambient pressure, P1 is approximately equal to P2 such that the fluid contained in inner membrane 405 remains therein. Upon the initiation of pressure from pressure source 402, P1 is greater than P2 causing fluid to flow from the interior of the inner membrane 405 to the delivery mechanism 403. With P1 greater than P2, the inner membrane 405 continues to collapse until all of the fluid contained therein passes to the delivery mechanism 403. Accordingly, a dosage of fluid equal to the internal volume of the inner membrane 405 is delivered to the delivery mechanism 403 and subsequently to the treatment site. FIG. 18A illustrates the condition where P1 equals P2 and FIG. 18B illustrates the condition where P1 is greater than P2.

The inner membrane 405 may be prepped (i.e., prepared for use) by pulling vacuum using pressure/vacuum source 402 while the delivery mechanism 403 is submerged in a drug solution. Alternatively, as illustrated in FIG. 18C, a prep lumen 406 may be provided to introduce the fluid into the inner membrane 405. The proximal end of the prepping lumen 406 is connected to a drug source 408 which contains the drug to be delivered to the treatment site. The distal end of the prepping lumen 406 is connected to a one-way valve 407 which is in fluid communication with the interior of the inner membrane 405. One-way valve 407 permits fluid to flow from the drug source 408 through the prepping lumen 406 and into the interior of the inner membrane 405, but does not permit fluid to flow from the interior of the inner membrane 405 back to the drug source 408.

In this manner, when a vacuum is applied using pressure/vacuum source 402, P1 is less than P2 causing fluid to flow from the drug source 408 through the prepping lumen 406 past the one-way valve 407 and into the interior of the inner membrane 405. Alternatively, the inner membrane 405 may be prepped by applying a positive pressure at the drug source 408 such that P3 is greater than P2. Upon the actuation of positive pressure from pressure source 402, P1 becomes greater than P2 causing fluid to flow from the interior of the inner membrane 405 past the one-way valve 407 (which does not permit fluid to flow into the prepping lumen 406) and into the delivery mechanism 403.

Refer now to FIG. 18D which illustrates an alternate embodiment utilizing an inner membrane comprising multiple sections 405A, 405B and 405C having different physical properties. Although three discrete sections of the inner membrane 405 are illustrated in FIG. 18D, it is contemplated that two, three, or more sections may be utilized. Each of the sections of the inner membrane 405 have a different physical construction such that each section collapses at a different pressure. The geometry (length, I.D., O.D. and wall thickness) and/or the material properties (e.g., durometer) may be selected to cause the section to collapse at a desired pressure.

For example, the discrete sections 405A, 405B and 405C of the inner membrane 405 may have the same geometry (length, diameter and wall thickness) while having different durometers. Section 405A may have a low durometer while section 405B has an intermediate durometer and section 405C has a relatively high durometer. With this arrangement, section 405A of the inner membrane 405 will collapse at a relatively low pressure thus causing fluid to flow from the interior of section 405A to the delivery mechanism 403. At a relatively higher pressure, section 405B will collapse thus delivering an additional amount of fluid equal to the interior volume of the section 405B to the delivery mechanism 403. At yet a higher pressure, section 405C will collapse thus delivering the remainder of the fluid to the delivery mechanism 403. With this arrangement, it is possible to selectively deliver precise amounts of fluid from the inner membrane 405 to the delivery mechanism 403 by varying the pressure from source 402.

Alternatively, each discrete inner membrane section 405$a$, 405$b$, 405$c$ may be formed of the same material but have varying wall thickness. Section 405$a$ may have a relatively thin wall whereas section 405$b$ may have a relatively thick wall and section 405$c$ may have an even thicker wall. With this arrangement, section 405$a$ will collapse at a relatively low pressure delivering a volume of fluid equal to the interior volume of section 405$a$ to the delivery mechanism 403. At a relatively higher pressure, section 405$b$ will collapse delivering a volume of fluid equal to the interior volume of section 405$b$ to the delivery mechanism 403. At yet an even high pressure, section 405$c$ will collapse causing fluid to flow from the interior of section 405$c$ to the delivery mechanism 403. In this matter, it is possible to deliver discrete amounts of fluid to the delivery mechanism 403 at preselected pressures.

In addition, by varying the length of each section, a different amount of fluid may be contained in each delivered at each preselected pressure. Those skilled in the art will recognize the varying other physical aspects of the inner membrane sections 405$a$, 405$b$ and 405$c$ may be utilized to accomplish the same result. In each instance, however, it is desirable to have the internal volume of the inner membrane 405 in the collapsed state be substantially equal to zero in order to minimize the residual fluids remaining inside the inner membrane 405 after drug delivery.

Refer now to FIG. 18E which illustrates yet another embodiment utilizing a torque mechanism 409 to affect the collapse of inner membrane 405. Torque mechanism 409 may be accomplished by a simple digital manipulation by the treating physician or other suitable alternative. As the inner membrane 405 is rotated by the torque mechanism 409, the internal volume of the inner membrane 405 is reduced. Each rotation of the inner membrane 405 causes a discrete reduction in the internal volume of the inner membrane 405 thus delivering a discrete amount of fluid to the delivery mechanism 403 and subsequently to the treatment site. Preferably, the inner membrane 405 is rotated until all of the fluid contained therein flows to the delivery mechanism 403 thus minimizing the residual fluid after drug delivery. It is also contemplated that the torque mechanism 409 may be used in conjunction with the pressure source 402, utilizing each to deliver the desired amount of fluid to the delivery mechanism 403.

Refer now to FIG. 18F which illustrates the use of a tension mechanism 410 which longitudinally stretches the inner membrane 405 to displace fluid therein to the delivery mechanism 403. As tension is selectively applied to the inner membrane 405 by tension mechanism 410, a predefined amount of fluid is displaced to the delivery mechanism 403, proportional to the amount of displacement of the tension mechanism 410. With this arrangement, controlled amounts of fluid may be delivered from the interior of the inner membrane 405 to the delivery mechanism 403 and thereafter to the treatment site by selectively displacing the proximal end of the inner membrane 405 using tension mechanism 410. The amount of fluid delivered to the delivery mechanism is a function of the longitudinal displacement of the proximal end of the inner membrane 405.

It is also contemplated that the tension mechanism 410 may be used in conjunction with the pressure source 402 to deliver discrete amounts of fluid to the delivery mechanism 403. It is further contemplated that the rigid outer member 404 may be omitted from the embodiments illustrated in FIGS. 18E-18G if a pressure source 402 is not utilized.

Figure 18G:
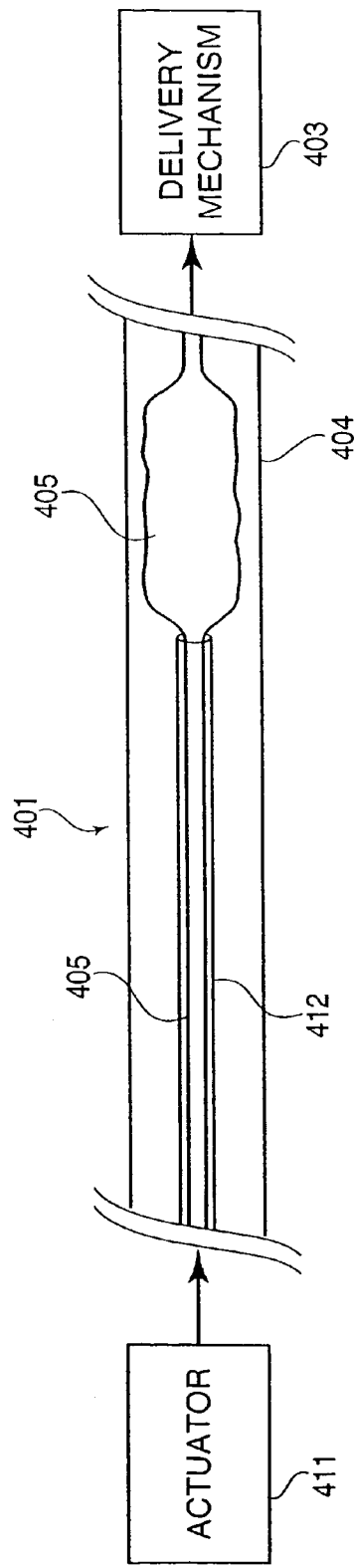

Refer now to FIG. 18G which illustrates yet another embodiment utilizing an annular die 412 to squeeze the inner membrane 405 thus displacing fluid disposed in the inner membrane 405 to the delivery mechanism 403. The annular die 412 may be advanced and/or retracted using an actuator 411. The actuator 411 may be accomplished by manual operation or any suitable alternative. With this arrangement, advancement of the die 412 squeezes the inner membrane 405 and pushes fluid out in an amount proportional to the length of the advancement of the die 412. Accordingly, discrete amounts of fluid may be delivered from the inside of the inner membrane 405 to the delivery mechanism 403 by actuating the annular die 412 in discrete lengths. As with the embodiments depicted in FIGS. 18E and 18F, it is contemplated that the actuator 411 may be used in combination with the pressure source 402. Alternatively, the actuator 411 may be used alone in which case the outer member 404 is not necessary.

Figure 18H:
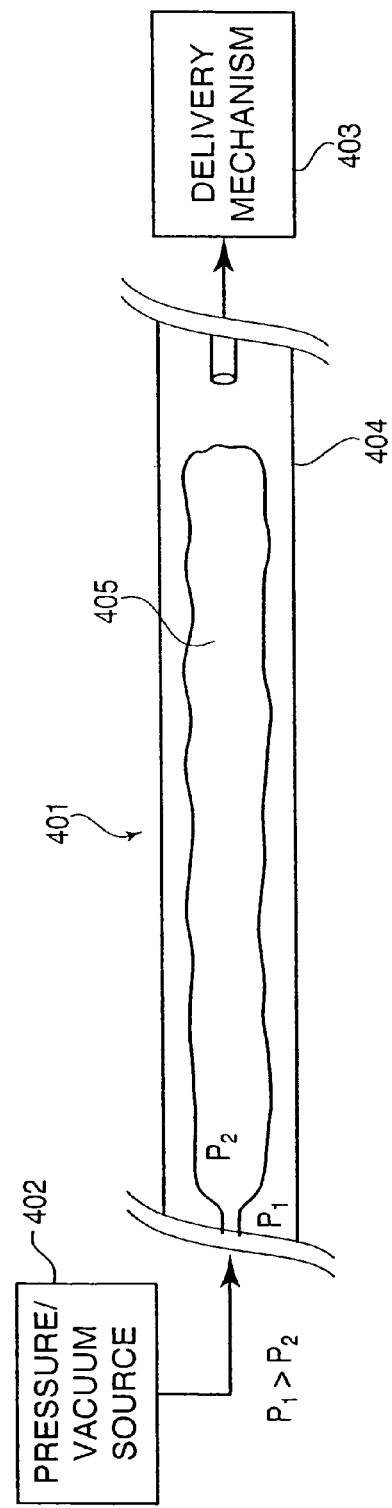

Refer now to FIG. 18H which illustrates an alternative embodiment of the present invention wherein the therapeutic fluid is contained between the outer member 404 and the inner membrane 405. This embodiment is similar to the embodiment illustrated in FIGS. 18A and 18B, except that the pressure/vacuum source 402 is in fluid communication with the inside of the inner membrane 405, and the delivery mechanism 403 is in fluid communication with the space located between the outer member 404 and the inner membrane 405. When pressure is applied to the inside of the inner membrane by pressure source 402, the pressure $P_2$ therein is greater than pressure $P_1$ between the outer member 404 and the membrane 405. This causes fluid to flow from the intersticial space and into the delivery mechanism 403, and ultimately to the treatment site. This embodiment, as illustrated in FIG. 18H, may incorporate some of the same features illustrated in FIGS. 18C and 18D. In particular, a prepping lumen 406 may be provided to introduce the therapeutic fluid into the intersticial space between the inner membrane 405 and the outer member 404. In addition, the inner membrane 405 may be separated into discrete sections having differing geometries and material characteristics.

Thus, it can be seen that the present invention provides a number of advantages over prior art infusion techniques. The present invention can be utilized to transluminally access a site to be treated within the body. The present invention can also be utilized to administer a therapeutic solution, or any desired solution, at that site. Further, the present invention can be utilized to administer only a very small volume bolus of material, preferably less than 1, milliliter at the site. Further, the present invention, in one preferred embodiment, utilizes a system with an overall dead space of less than 0.17 cc, including the dead space in the proximal manifold and the remainder of the catheter. This allows the pragmatic administration of even very expensive drugs in an efficient and accurate manner.

It should also be noted, of course, that the distal portion of the catheter can be arranged to provide any sort of nozzle configuration. The distal portion can be valved, it can simply have one or more apertures uniformly distributed thereabout, it can have apertures directionally distributed thereabout, and it can have apertures which provide desired injection or dispersion characteristics.

Although the present invention has been described with reference to preferred embodiments, workers skilled in the art will recognize that changes may be made in form and detail without departing from the spirit and scope of the invention.

What is claimed is:

1. A method of infusing a liquid at a treatment site, comprising:
    providing a catheter including an outer member with a lumen extending therethrough and an inner member defining a collapsible membrane within the lumen, the collapsible membrane having an interior fluidly connected to a delivery mechanism, the outer member being rigid relative to the inner member and the inner member being pliable relative to the outer member;
    introducing an infusate into the interior of the membrane;
    navigating the catheter through a body lumen to a treatment site;
    positioning the delivery mechanism at the treatment site, and
    applying a force to the collapsible membrane causing the membrane to collapse and thereby expel the infusate into the delivery mechanism and to the treatment site.

2. The method of infusing a liquid at a treatment site as in claim 1 wherein the force applied to the collapsible membrane comprises fluid pressure.

3. The method of infusing a liquid at a treatment site as in claim 1 wherein the force applied to the collapsible membrane comprises compression by a compression member.

4. The method of infusing a liquid at a treatment site as in claim 3 wherein the compression member comprises a die that squeezes the collapsible membrane.

5. The method of infusing a liquid at a treatment site as in claim 1 wherein the collapsible membrane comprises a plurality of discrete sections having different physical characteristics.

6. The method of infusing a liquid at a treatment site as in claim 5 wherein the physical characteristics are dimensions of the discrete sections.

7. The method of infusing a liquid at a treatment site as in claim 5 wherein the physical characteristics are material properties of the discrete sections.

8. The method of infusing a liquid at a treatment site as in claim 1 wherein the force applied to the collapsible membrane comprises compression by rotation of the collapsible membrane.

9. The method of infusing a liquid at a treatment site as in claim 1 wherein the force applied to the collapsible membrane comprises compression by stretching of the collapsible membrane.

10. A method of infusing a liquid at a treatment site, comprising:
    providing a catheter including an outer member with a lumen extending therethrough and an inner member comprising an inflatable membrane within the lumen, the outer member being rigid relative to the inner member and the inner member being pliable relative to the outer member;
    navigating the catheter through a body lumen to a treatment site;
    positioning the delivery mechanism at the treatment site;
    introducing an infusate into an area between the outer member and the inner member; and
    inflating the inflatable member to squeeze the area between the outer member and the inner member and thereby expel the infusate to the treatment site.

* * * * *